(12) United States Patent  
Akai et al.

(10) Patent No.: US 9,298,888 B2  
(45) Date of Patent: Mar. 29, 2016

(54) WEIGHT MANAGEMENT SYSTEM

(71) Applicant: KAO Corporation, Tokyo (JP)

(72) Inventors: Kanji Akai, Hoffman Estates, IL (US); Hideyo Nakamura, Champaign, IL (US); Paul Tutt, Kankakee, IL (US); Katherine Kleyn, Barrington, IL (US)

(73) Assignee: Kao Corporation, Tokyo (JP)

( * ) Notice: Subject to any disclaimer, the term of this patent is extended or adjusted under 35 U.S.C. 154(b) by 393 days.

(21) Appl. No.: 13/896,534

(22) Filed: May 17, 2013

(65) Prior Publication Data

US 2014/0344192 A1    Nov. 20, 2014

(51) Int. Cl.
 *G06N 5/00*   (2006.01)
 *G06F 1/00*   (2006.01)
 *G06F 19/00*  (2011.01)

(52) U.S. Cl.
 CPC ........ *G06F 19/3475* (2013.01); *G06F 19/3481* (2013.01)

(58) Field of Classification Search
 CPC ........... G06N 5/02; G06N 5/04; G06N 5/048; G06Q 10/00
 See application file for complete search history.

(56) References Cited

U.S. PATENT DOCUMENTS

2010/0216601 A1 *  8/2010  Saalasti et al. .................... 482/8
2014/0106312 A1 *  4/2014  Klein ............................ 434/127

FOREIGN PATENT DOCUMENTS

| JP | 2003-203123 | 7/2003 |
| JP | 2007-272761 | 10/2007 |
| JP | 2009-265791 | 11/2009 |

OTHER PUBLICATIONS

English Machine Translation of Japanese Patent No. JP 2003-203123.
English Machine Translation of Japanese Patent No. JP 2009-265791.
The Diabetes Prevention Program (DPP): Description of lifestyle intervention, 25 Diabetes care 2165-2171 (Dec. 2002).

* cited by examiner

*Primary Examiner* — Stanley K Hill
*Assistant Examiner* — Kalpana Bharadwaj
(74) *Attorney, Agent, or Firm* — Frost Brown Todd LLC

(57) ABSTRACT

A weight management system can be implemented which assists a user in losing a target amount of weight before the conclusion of a weight loss program. Such a system can assign the user to a behavioral segment, and may further assign the user to an attitudinal segment as well. The weight management system can provide recommendations for the user's diet and exercise based on health information provided by the user and the segment or segments to which the user is assigned. These recommendations can be updated during the course of the weight loss program based on the user's continued progress or lack of the same.

17 Claims, 17 Drawing Sheets

FIG. 3

| Gender | 1 | (Male:1/Female:2) |
| --- | --- | --- |
| Height | 72 | Inches → 182.88 cm |
| Weight | 260 | lb → 118.1818 kg |
| Age | 40 | years |

Weight: 250 lb → Goal Weight Loss: 18.2 lb (7%) → Weight Goal: 241.8 lb

↓ 182 days   Calories to be reduced per day 0.10 lb/day → 350 Calories
1 lb = 3500 Calories

BMR (HB): 2328
BMR (MJ): 2132

Total Energy Expenditure: 2771 Calories → Calories Budget per day: 2421 Calories BMRx1.3=TEE

| | Calories Budget | |
| --- | --- | --- |
| | Calorie-in | Calorie-out |
| Medicators | 2561 | 139 |
| Naturals | 2644 | 223 |
| Holistics | | |
| HCP Followers | 2658 | 237 |
| Health Food Focused | 2658 | 237 |
| Content All Rounders | 2700 | 279 |
| Exercise Focused | 2672 | 251 |

1. Calories burned=METSxWeight(kg)xTime(h)   <kg = lbs/2.2>
2. Moderate Walking = 3.3 METS
3. DPP Study: minimum 150 min/week for exercise
   Minimum Required Calories burned from Additional Physical Activities
   3.3 METSx1/3 hours (20 min) x weight
   x 2.5/7 hours
4. Coefficients of Exercise for each segment

| Medicators | 2.849622 | 1.0 |
| Naturals | 4.598201 | 1.6 |
| Holistics | 5.046476 | 1.8 |

| HCP Followers | 5.681027 | 1.7 |
| Health Food Focused | 5.839856 | 1.7 |
| Content All Rounders | 6.611936 | 2.0 |
| Exercise Focused | 5.944117 | 1.8 |

AVG. 6.019234

WEIGHT MANAGEMENT SYSTEM

FIELD

The disclosed technology can be used in the field of weight management, and is preferably applied in allowing a user to lose a predetermined amount of weight in a predetermined time.

BACKGROUND

Conventionally, when an individual wishes to improve his or her health or risk of obesity, it is recommended that the individual make changes to his or her diet. There exist a number of systems which can support a user who is on a diet to reach a weight loss target, such as disclosed in Japanese patent document JP 2003-203123 A and Japanese patent document JP 2009-265791 A. It is known that this type of goal directed weight loss can be particularly useful for individuals who have, or are at risk of developing, diabetes, as it has been found that a reduction of 7% of a person's body weight over an approximately six month (26 week) period can allow an individual who has or is at, risk of diabetes to reduce his or her symptoms or risk level. See, e.g., The Diabetes Prevention Program (DPP): Description of lifestyle intervention, 25 Diabetes Care 2165-2171 (December 2002) (hereinafter "DPP").

While there are weight management systems in the prior art, these systems are generally deficient in one way or another. For example, the weight management systems of Japanese patent document JP 2003-203123 A and Japanese patent document JP 2009-265791 A fail to provide ongoing user support functions such as checking the status of a user's progression to a weight loss goal. Additionally, currently used technology does not provide an effective way to tailor recommendations, particularly exercise recommendations, to users without involving a skilled professional who can personally create a recommendation for a user or requiring complicated and often unreliable determinations made on a user by user basis. Accordingly, there is a need in the art for an improved weight management system, and, in particular for a weight management system which can tailor recommendations in a manner which is more effective than has heretofore been available, which can provide ongoing user support functions such as checking the status of a user to a weight loss goal, or both.

SUMMARY

The teachings of this disclosure can be used in a variety of manners, including implementing a weight management system which can comprise elements such as a data storing unit, a calorie to be reduced calculating unit, a caloric balance calculating unit, a caloric balance setting unit, and an information presentation unit. In such a system, the data storing unit can be used to store input data provided by a user in response to a questionnaire which can be presented to the user either at initiation of a weight loss program, during the weight loss program, or both. A calorie to be reduced calculating unit can be implemented to determine, based on the weight of a user, a target amount of weight to lose by the completion of a weight loss program. A calorie to be reduced calculating unit can, alternatively or additionally, be implemented to calculate a daily weight loss goal consistent with achieving the target weight loss by the completion of the weight loss program. A caloric balance calculating unit can be implemented to, based on data stored by the data storing unit, calculate a base metabolism and total energy expenditure of the user. Such a caloric balance calculating unit could also calculate a recommended daily caloric balance based on the total energy expenditure and a weight loss goal, such as a daily weight loss goal which could be calculated by the calorie to be reduced calculating unit. The caloric balance setting unit could then be implemented to set a daily recommended exercise amount and a recommended meal calorie amount consistent with the daily recommended caloric balance. The information presentation unit could then be used to present the daily recommended exercise amount and the recommended meal calorie amount to the user of the weight management system.

Of course, the teachings set forth herein are susceptible of being implemented in forms other than the weight management system described above. For example, based on the teachings of this disclosure, one of ordinary skill in the art could implement other machines, methods, and articles of manufacture which could be used to assist users in identifying and reaching a weight loss goal within a predetermined period. Accordingly, the exemplary weight management system described above should be treated as being illustrative only, and should not be treated as implying limitations on the scope of any claims included in this or any related document.

BRIEF DESCRIPTION OF THE DRAWINGS

The drawings and detailed description which follow are intended to be illustrative only, and should not be treated as implying limitations on the scope of protection accorded by this or any related document.

FIG. 3 shows potential calculations which could take place in a system implemented according to this disclosure and example data on which those calculations could be performed.

DETAILED DESCRIPTION

The inventors have conceived of novel technology which, for the purpose of illustration, is disclosed herein as applied to the context of allowing an individual who has diabetes, or is at risk of developing diabetes, to lose 7% of his or her body weight within approximately six months (26 weeks). While the application of the inventors' technology within that context satisfies a long felt but unmet need in the art, it should be understood that the disclosure of the inventors' technology in that context is not intended to imply limitations on fields and applications in which the inventors' technology could be beneficially used. Accordingly, the disclosure set forth herein should be understood as being illustrative only, and should not be treated as limiting.

Figure 1:
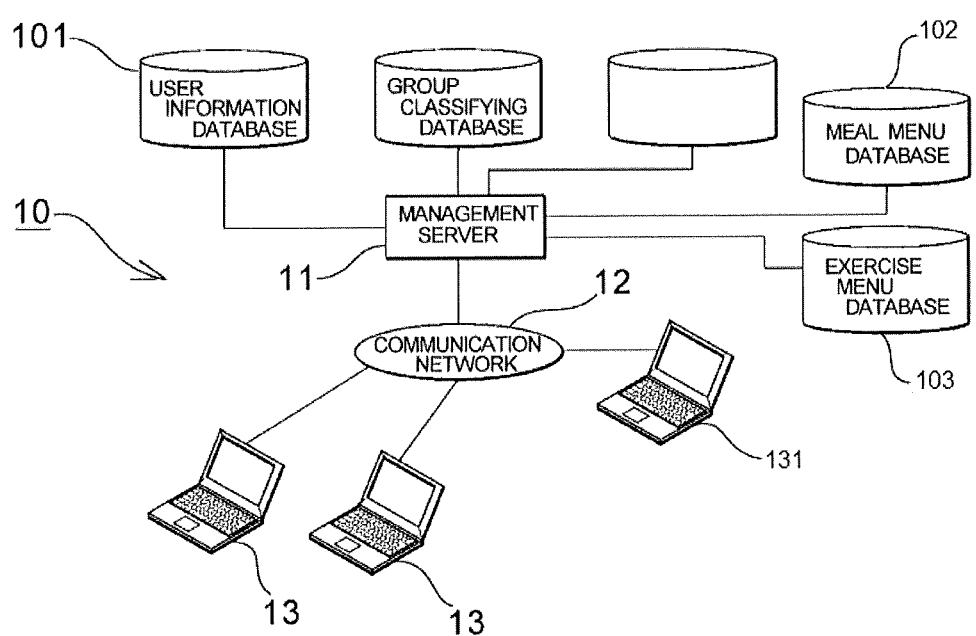
FIG. 1 depicts an exemplary weight management system which could be implemented based on the teachings of this document.

Turning now to the figures, FIG. 1 depicts a high level view of a weight management system [10] which could be implemented based on the teachings of this disclosure. As depicted in that figure, such a weight management system [10] could include a management server [11] which can allow a user to interact with the weight management system via a website accessible over a communication network [12] through one of a plurality of user terminals [13] (e.g., via a browsers operating on the user terminals). Such a weight management system [10] could also include an administrator terminal [131], which could similarly interact with the management server [11] via the website and communication network [12], though the interfaces presented to the administrator terminal [131] by the website may be different from, and support different functionality than, those presented to users using the user terminals [13].

Figure 2:
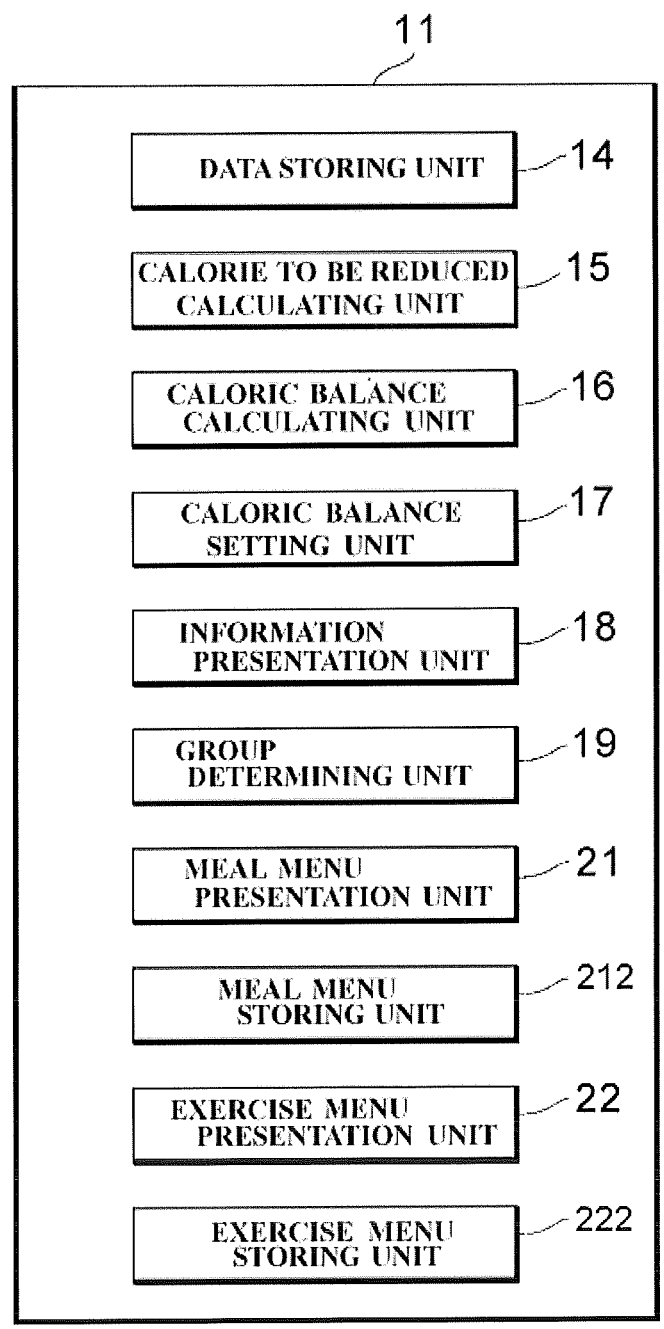
FIG. 2 depicts an exemplary management server that could be implemented in the context of a weight management system.

Continuing, FIG. 2 depicts an exemplary management server [11] which could be included in a weight management system [10] implemented according to FIG. 1. This exemplary management server [11] is configured to act as a server computer and to execute one or more computer programs to provide the functions of a data storing unit [14], a calorie to be reduced calculating unit [15], a caloric balance calculating unit [16], a caloric balance setting unit [17], an information presentation unit [18], a group determining unit [19], a meal menu presentation unit [21], a meal menu storing unit [212], an exercise menu presentation unit [22], and an exercise menu storing unit [222]. Each of these components is discussed in more detail below. It should be understood that, while the management server [11] of FIG. 2 is illustrated as including each of the listed components, this is not a requirement for weight management systems, whether implemented according to FIG. 1 or otherwise. Different or fewer components, or different combinations of components could also be included based on the requirements of a particular situation. Accordingly, neither the management server [11] of FIG. 2, nor the discussion of the components of that server set forth below should be understood as implying limitations on a weight management system implemented according to this disclosure.

Turning now to the individual components depicted in FIG. 2, the first of those components, the data storing unit [14] can be used to store data provided by a user at the time of initiating a weight loss program, potentially augmented by further data provided by the user as the program progresses. Preferably, a weight management system [10] implemented based on this disclosure will begin a weight loss program by presenting a user a questionnaire (e.g., via a website) requesting health data such as but not limited to the user's weight, age/date of birth, gender, and height. Such a questionnaire could also present the user with questions to determine a population segment to which the user could be assigned for purposes of determining recommendations on food intake and exercise for the user. Subsequently, during the course of the weight loss program, further information could be requested, such as the type of exercise performed by the user, the amount and frequency of each type of exercise performed by the user, the size of meals eaten by the user, the type of meals eaten by the user, and/or the user's blood glucose level. A data storing unit [14] such as shown in FIG. 2 could be used to store this data, such as by storing it in a user information database [101] or other suitable storage device.

Of course, while the above description of information which could be stored by a data storing unit [14] described a separation between information which would be requested at the initiation of a weight loss program, and information which would be requested while the weight loss program was ongoing, it should be understood that there could be some overlap between these two types of information as well. For example, in addition to being asked for his or her weight at the initiation of the weight loss program, the user may also be asked to input his or her current weight one or more times as the weight loss program progresses. These requests for the user's weight (and/or other information, such as exercise type and frequency, meal size and type, and blood glucose level) during the weight loss program will preferably be made on a repeated basis. Ideally, the information will be provided daily by the user. However, it is also possible that it could be provided less frequently, such as on a weekly basis, or at the time of a status update (which, in the preferred embodiment, will take place every four weeks). All such information could then be stored by the data storing unit [14], such as by storing it in a user information database [101] or other suitable storage device.

The next component illustrated in FIG. 2, the calorie to be reduced calculating unit [15], can calculate a target weight to be reached by the user at the end of a set time period, and can also be used to perform related calculations, such as calculating daily weight loss targets in the form of calories to be reduced per day by the user during the weight loss program. As a concrete example, consider the data provided in FIG. 3, which shows potential calculations which could take place in a system implemented according to this disclosure. With that data, a calorie to be reduced calculating unit [15] could calculate that a 260 pound (118 kg) man should lose 18.2 pounds (8.26 kg) by the end of a 26 week weight loss program by multiplying 260 pounds (118 kg) by a 7% body mass weight loss target. This 18.2 pound (8.26 kg) figure could then be subtracted from the original 260 pounds (118 kg) to obtain a 241.8 pound (109.7 kg) target weight for the end of the weight loss program. Similarly, since the weight loss program is to extend for a period of 26 weeks*7 days/week=182 days, a daily weight loss figure of 0.1 pounds (0.045 kg) per day can be determined by dividing the 18.2 pound (8.26 kg) weight loss goal by the number of days in the weight loss program.

This can then be converted to calories to be reduced per day by multiplying the number of pounds (kilograms) by the number of calories in a pound (i.e., 3,500) or number of calories in a kilogram (i.e., 7,700), resulting in figure of about 350 calories to be reduced per day.

Of course, these calculations can be performed both at the initiation of a weight loss program as well as during the program's duration. For example, the calorie to be reduced calculating unit [15] can initially calculate the amount of weight to be lost during the weight loss program and an amount of calories to be reduced per day based on information from the user's initial questionnaire. It could then recalculate the daily calories to be reduced to meet the weight loss target one or more times during the weight loss program based on data subsequently provided by the user. The results of these calculations, and the results of the initial calculations, can then be stored by the data storing unit [14] (e.g., in a user information database [101]).

The next component illustrated in FIG. 2 is the caloric balance calculating unit [16]. Such a component can be used to calculate the user's base metabolism and total energy expenditure based on information stored by the data storing unit [14] (e.g., the user's weight, height and age), and, in some implementations, could also be used to calculate a daily recommended caloric balance from the calculated total energy expenditure and the calories to be reduced per day. This can be done by, initially, calculating the user's base metabolism using formulas based on information provided for the user, such as the user's age, gender, weight and height. The user's total energy expenditure can then be calculated by multiplying this base metabolism by 1.3 (it should be noted that this figure is given as the technology is described in the context of users who have or are at risk of developing diabetes, but that implementations used for other purposes may use different, or varying, coefficients to account for the fact that total energy expenditure may vary according to other factors, such as the activity level of the user). The daily recommended caloric balance may then be calculated by subtracting the calories to be reduced calculated by the calorie to be reduced calculating unit [15] from the calculated total energy expenditure. Further, after the recommended caloric balance has been calculated, in some implementations, a check can then be performed to verify that the daily recommended caloric balance is greater than the user's base metabolic rate. In such implementations, the recommended caloric balance is less than the user's base metabolic rate, the recommended caloric balance could be set equal to the user's base metabolic rate, effectively setting the base metabolic rate as a floor for the recommended caloric balance.

A concrete example of calculations which could be performed by a caloric balance calculating unit [16] is provided in FIG. 3. As shown in that figure, if the information for a user indicates that the user is a 40 year old man with a height of 72 inches (approximately 1.83 meters) and a weight of 260 pounds (118 kg), his base metabolism can be calculated at 2,132 calories in accordance with a BMR formula by Mifflin-St. Jeor (other formulas, such as a general BMR operation formula from Harris Bendict, which would calculate base metabolism in this case as 2,328 calories could also be used, though these other formulas are not utilized in the preferred embodiment). Using this base metabolism, total energy expenditure can be obtained by multiplying 2,132 by 1.3, resulting in a total energy expenditure figure of 2,771 calories. A daily recommended caloric balance of 2,421 calories can then be calculated by subtracting the figure of 350 calories to be reduced per day previously determined by the calorie to be reduced calculating unit [15] from the total energy expenditure of 2,771 calories. This can then be used as the daily recommended caloric balance necessary to achieve the target weight by the end of the weight loss program.

Of course, as with the calculations described above in the context of the calorie to be reduced calculating unit [15], some or all of the calculations performed by the caloric balance calculating unit [16] could be performed both at the initiation of a weight loss program, and one or more times during the weight loss program itself. For example, the caloric balance calculating unit [16] can initially calculate the user's base metabolism, total energy expenditure and daily recommended caloric balance based on information from the user's initial questionnaire and information originally determined by the calorie to be reduced calculating unit [15]. These values could subsequently be recalculated one or more times during the weight loss program based on data subsequently provided by the user and on subsequent calculations of the calorie to be reduced calculating unit [15]. The results of these calculations, and the results of the initial calculations, can be stored by the data storing unit [14] (e.g., in a user information database [101]).

The management server [11] of FIG. 2 also includes a group determining unit [19]. Such a group determining unit [19] could be used, for example, to match users of the weight management system [10] with population segments which had been defined in advance based on behavioral and attitudinal factors identified as significant for a weight loss goal (e.g., reduction of the symptoms or risk of diabetes). To illustrate, consider a group determining unit [19] in a weight management system [10] adapted to facilitate the reduction of symptoms or risk of diabetes. Such a group determining unit [19] could determine whether a user belongs to the behavioral segments of medicators (i.e., individuals who manage their health, or, in this case, diabetes or risk of developing the same, primarily through medication), naturals (i.e., individuals who actively manage their health, or, in this case, diabetes or risk of developing the same, through diet and exercise), and holistics (i.e., individuals who use diet, exercise and medication to manage their health, or, in this case, diabetes or risk of developing the same).

For users determined to belong to the behavioral segment of holistics, a further determination could be made as to whether the users belong to an attitudinal segment of health care professional (HCP) followers (i.e., individuals who actively manage their health, or, in this case, diabetes or risk of developing the same, through medication with a lesser focus on diet and exercise), health food focused (i.e., individuals who actively manage their health, or, in this case, diabetes or risk of developing the same, through diet with a lesser focus on exercise and medication), content all rounders (i.e., individuals who use a truly holistic approach to managing their health, or, in this case, diabetes or risk of developing the same, using diet, exercise and medication), and exercise focused (i.e., individuals who actively manage their health, or, in this case, diabetes or risk of developing the same, through exercise with a lesser focus on diet and medication). This determination could be made based on information provided by the user, such as in response to an initial questionnaire completed when initiating a weight loss program, and could be stored, along with other information, by the data storing unit [14] (e.g., in the user information database [101]).

Figure 17:
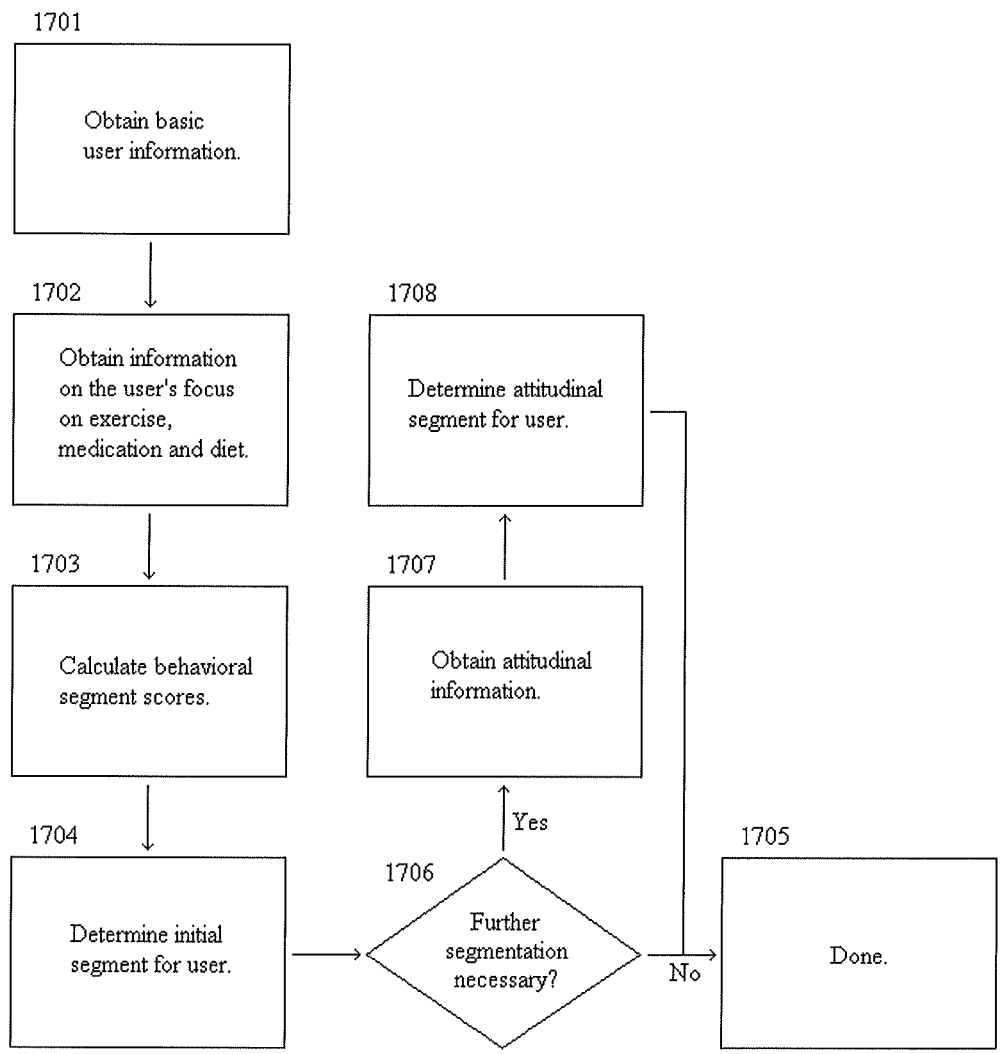
FIG. 17 depicts an exemplary process which could be used in segmenting users.

As a further illustration of how a group determining unit [19] could potentially be used in, and integrated with, a weight management system [10], consider the method depicted in FIG. 17. Initially, in a method following the process of FIG. 17, a weight management system [10] would obtain basic information about a user [1701], such as the user's gender, height, weight and age. This information could be obtained via a questionnaire presented to the user, as described previously, but could also be obtained in other manners, such as by requesting the information from an individual who is familiar with, but not necessarily the same as, the person who would utilize the weight management system (e.g., a personal trainer, or physician). The method could then continue with the weight management system obtaining (perhaps via the same questionnaire as the health information) information on the user's focus on exercise, medication and diet [1702] when managing health issues. For example, a questionnaire could be presented which would request that the user indicate, on a scale of 1-7, how often he or she (or the person who will be using the weight management system [10] for weight loss) uses the following techniques to manage his or her risk or symptoms of diabetes:

Exercise [1 means never, 2 means once a month, 3 means more than once a month but less than once a week, 4 means 1-2 times per week, means 3-4 times per week, 6 means 5-6 times per week, an 7 means every day]

Diet [1 means never, 4 means sometimes, and 7 means at every meal]

Medication [1 means I do not take medication, 4 means I sometimes take my medication, and 7 means I always take medication as directed].

Once the system has obtained the information on the user's focus on exercise, medication and diet [1702], the method of FIG. 17 can proceed with the calculation of behavioral segment scores [1703]. For example, if the user was requested to score his or her focus on exercise, diet and medication on a one to seven scale, the scores provided by the user could be used to calculate scores for the segments of medicators, holistics and naturals as follows:

$$M_s = 2.85*E + 3.02*D + 13.48*M_f + -55.38$$

$$H = 5.05*E + 4.12*D + 14.27*M_f + -74.47$$

$$N = 4.6*E + 4.61*D + 3.17*M_f + -26.94$$

where $M_s$ is the user's medicators segment score, H is the user's holistics segment score, N is the user's naturals segment score, E is the user's exercise focus score, D is the user's diet focus score, and $M_f$ is the user's medication focus score. These scores could then be used to determine an initial segment for the user [1704]. For example, the medicator segment score, holistics segment score and naturals segment score could be compared, and the user assigned to the medicators, holistics or naturals segment based on which of the scores was highest.

After the initial segmentation [1704] had taken place, the process of FIG. 17 could terminate [1705] if a check [1706] revealed that no further segmentation was necessary. Alternatively, if the check [1706] revealed that further segmentation was necessary (e.g., in the example above, if the user was assigned to the holistics segment), information, referred to for convenience as attitudinal information, could be obtained regarding traits such as the user's belief that he or she could do more to manage his or her problems related to weight (which, in the exemplary embodiment, would be the user's risk or symptoms of diabetes), the importance he or she places on natural or organic ingredients for food, his or her compliance with instructions from health care professionals, his or her actual or perceived lack of time to implement a behavior change, and his or her perception of behavior changes since learning of a weight loss issue (which, in the exemplary embodiment, would correlate to the user being diagnosed as having, or being at risk for developing, diabetes) [1707]. For example, the user could be presented with a questionnaire asking him or her to indicate his or her agreement or disagreement with each of the following statements on a scale one to seven, where one means strongly disagree and seven means strongly agree:

| | |
|---|---|
| $S_1$ | I feel I could do more to better manage my diabetes. |
| $S_2$ | I buy the brand that has natural/organic ingredients. |
| $S_3$ | I always do as my doctor advises. |
| $S_4$ | I am too busy to change my diet. |
| $S_5$ | Since being diagnosed I exercise more frequently. |

Once the attitudinal information had been obtained, the process of FIG. 17 could continue by using that information, potentially in combination with the focus information obtained previously [1702] to determine an attitudinal segment for the user [1708]. This could be done in a manner similar to that described above for the determination of the initial segment [1704], with scores being calculated for each attitudinal segment and the user assigned to the attitudinal segment with the highest score. A set of exemplary equations which could be used for this purpose, when a user is to be assigned to a HCP follower, health food focused, content all rounders or exercise focused attitudinal segment after being initially assigned to a holistics behavioral segment is set forth below in table 1.

TABLE 1

Exemplary equations for determining scores for attitudinal segments.

HCP = 5.68 * E + 3.46 * D + 57.81 * $M_f$ + 5.23 * I + −1.32 * O + 0.26 * A + 1.66 * B + −1.23 * F + −240.89
HFF = 5.84 * E + 3.42 * D + 56.77 * $M_f$ + 5.63 * I + −0.28 * O + −0.55 * A + 1.12 * B + −0.72 * F + −237.3
COR = 6.61 * E + 3.96 * D + 56.02 * $M_f$ + 3.24 * I + −0.67 * O + 0.07 * A + 1.28 * B + −0.23 * F + −230.81
EF = 5.94 * E + 3.57 * D + 55.99 * $M_f$ + 5.47 * I + −0.82 * O + −0.74 * A + 1.89 * B + 0.03 * F + −234.878

In the equations of table 1, HCP is the user's HCP followers score, HFF is the user's health food focused score, COR is the user's content all rounder's score, I is the user's score corresponding to the trait measured by his or her agreement with statement $S_1$ above, O is the user's score corresponding to the trait measured by his or her agreement with statement $S_2$ above, A is the user's score corresponding to the trait measured by his or her agreement with statement $S_3$ above, B is the user's score corresponding to the trait measured by his or her agreement with statement $S_4$ above, F is the user's score corresponding to the trait measured by his or her agreement with statement $S_5$ above, and the remaining variables (E, D and $M_f$) have the same meanings as set forth above in the context of the initial segmentation. Once the user's attitudinal segment had been determined [1708], the process of FIG. 17 could then terminate [1705], with no further segmentation being performed.

Of course, it should be understood that the process of FIG. 17 is intended to be illustrative only, and that variations on that process and the accompanying discussion could be used in weight management systems [10] or group determining units [19] implemented according to this disclosure. For example, the discussion above described a sequence of events in which information used in segmenting users was obtained in multiple stages (i.e., two steps [1702][1707] in the method of FIG. 17). However, it is possible that these stages could be collapsed into one, such as by asking all users the same set of questions, but treating the answers to those questions differently depending on how far along the segmentation for a particular user has progressed (e.g., if it is determined that no segmentation beyond the initial segmentation is necessary, then answers to questions which are relevant only to segmentations after the initial segmentation could be disregarded). It is also possible that additional stages could be added. For example, after determining an attitudinal segment, rather than terminating, a method such as shown in FIG. 17 could return to the check of whether further segmentation is necessary, thereby allowing the weight management system to support arbitrarily precise segmentation for its users.

It is also possible that the approach to determining the segment (or segments) for the user could vary from that described in the context of FIG. 17. For example, rather than combining the scores for different behavioral and attitudinal traits into scores for different segments, the user could be asked questions whose answers would directly indicate what segment (or segments) he or she should be placed in. It is also possible that different numbers (e.g., more or fewer segments than those discussed in the exemplary embodiment) or structures (e.g., only a single level of segmentation, rather than an initial level of segmentation followed by identification of subsegments) of segments might be used. Accordingly, even in systems implemented using the inventor's technology where segmentation takes place, the discussion set forth above should be understood as being illustrative only, and should not be treated as implying limitations on the protection accorded by this or any related document.

Continuing with the discussion of the components of FIG. 2, the caloric balance setting unit [17] can set a daily recommended exercise amount and recommended daily meal caloric amount for the user to achieve his or her desired weight loss by the conclusion of the weight loss program. This can be done using a two step process beginning with identifying the daily recommended exercise amount by taking a pre-defined minimum exercise amount, determining the number of calories burned per day by someone having the user's weight in performing that minimum exercise amount, then applying an exercise modification factor (e.g., by multiplying the resulting figure by an exercise coefficient) determined based on the population segment identified for the user by the group determining unit [19] to obtain the recommended daily exercise amount. The daily recommended exercise amount could then be added to the recommended daily caloric balance calculated by the caloric balance calculating unit [16] to obtain the recommended daily meal caloric amount.

As a concrete illustration of how a caloric balance setting unit [17] could operate, consider how these calculations could take place using the data from FIG. 3. As shown in that figure, the minimum calorie amount can be calculated as approximately 139 calories, using the equation $C_{out}$=3.3 METS*118 kg*2.5 hours/7 days. In that equation, $C_{out}$ is the minimum amount of exercise to be done per day, measured in calories. 3.3 METS is a measure of the intensity of the recommended exercise (in this case, moderate walking), and shows that, when doing the recommended exercise, a user will use energy 3.3 times faster than when he or she is at complete rest. 118 kg is the weight of the user (which, if originally entered by the user in pounds, could be converted to kilograms by dividing it by 2.2). 2.5 hours/7 days is the minimum amount of time the user is assumed to spend on the recommended exercise per day. In the exemplary calculation, this is presumed to be 150 minutes/week of moderate walking. However, other values, such as 20 minutes/day, or values between 150 minutes/week and 20 minutes/day, could also be used, depending on the context and observed or hypothesized characteristics of the population in which the technology is deployed.

In this example, after the minimum daily exercise amount of 139 calories is calculated, a recommended daily exercise amount is determined based on stored coefficients of exercise associated with each of the pre-defined user segments. As shown in FIG. 3, in the preferred embodiment, these coefficients are 1.0 for medicators, 1.6 for naturals, 1.7 for those holistics identified as HCP followers or as health food focused, 2.0 for those holistics identified as content all rounders, and 1.8 for those holistics identified as exercise focused. Using these coefficients, if the user is in the medicators segment, his or her recommended daily exercise amount can be calculated as 139 calories. If the user is in the naturals segment, his or her recommended daily exercise amount can be calculated as 223 calories. If the user is in the HCP followers segment, his or her recommended daily exercise amount can be calculated as 237 calories. If the user is in the health food focused segment, his or her recommended daily exercise amount can be calculated as 237 calories. If the user is in the content all rounders segment, his or her recommended daily exercise amount can be calculated as 279 calories, and if the user is in the exercise focused segment, his or her recommended daily exercise amount can be calculated as 251 calories.

These recommended daily exercise amounts can then be added to the user's recommended daily caloric balance (i.e., 2,421 calories in the example calculations of FIG. 3) to obtain the user's recommended daily meal amount. As a result, if the user is in the medicators segment, his or her recommended daily meal amount can be calculated as 2,561 calories. If the user is in the naturals segment, his or her recommended daily meal amount can be calculated as 2,644 calories. If the user is in the HCP followers segment or the health food focused segment, his or her recommended daily meal amount can be calculated as 2,658 calories. If the user is in the health content all rounders segment, his or her recommended daily meal amount can be calculated as 2,700 calories, and if the user is in the exercise focused segment, his or her recommended daily meal amount can be calculated as 2,672 calories.

Variations are also possible. For example, while in a preferred embodiment, all holistics will be classified into attitudinal segments, it is possible that the technology disclosed herein could be implemented so that this additional classification might not be applied all (or any) holistics. In such a case, as shown in FIG. 3, it is possible that similar calculations can be performed using a coefficient of 1.8 for a user in the holistics segment who is not further categorized as a HCP follower, health food focused, a content all rounder, or exercise focused. In such a case, and using the data shown in FIG. 3, a user identified simply as a holistic would have a recommended daily exercise amount of about 251 calories, and a daily recommended meal amount of 2,672 calories.

Of course, as with the calculations described above in the context of the calorie to be reduced calculating unit [15] and the caloric balance calculating unit [16], some or all of the calculations performed by the caloric balance setting unit [17] could be performed both at the initiation of a weight loss program, and one or more times during the weight loss program itself. For example, the caloric balance setting unit [17] could initially calculate the recommended daily exercise and meal amounts based on the recommended caloric balance initially calculated by the caloric balance calculating unit [16], and could later recalculate these values in the event the caloric balance calculating unit [16] calculates a new recommended daily caloric balance during the course of the weight loss program. The results of these calculations, and the initial calculations, like the other results described herein, could then be stored by the data storing unit [14] (e.g., in a user information database [101]).

In addition to being stored by a data storing unit [14], values calculated by a weight management system [10], potentially accompanied by some or all of the underlying data, could also be presented to a user, such as by an information presentation unit [18], shown in FIG. 2 as a component of the management sever [11]. To illustrate how this could take place, consider a situation in which a weight management system [10] was used by users who would enter initial data based on a questionnaire as described above and would enter updated data throughout the course of the weight loss program. Ideally, this updated data would include both the users' weight and what exercises they performed on a daily (or even more frequent) basis though, as discussed in more detail below, this is not a requirement. In such a situation, the information presentation unit [18] could be used to provide periodic (e.g., every four weeks) status updates during the course of the weight loss program, and to inform the users of any new or revised recommendations which might be necessary or appropriate based on the data entered subsequent to completion of the initial questionnaire. FIGS. 4-16 provide examples of interfaces which could be presented to users in such a situation.

Figure 4:
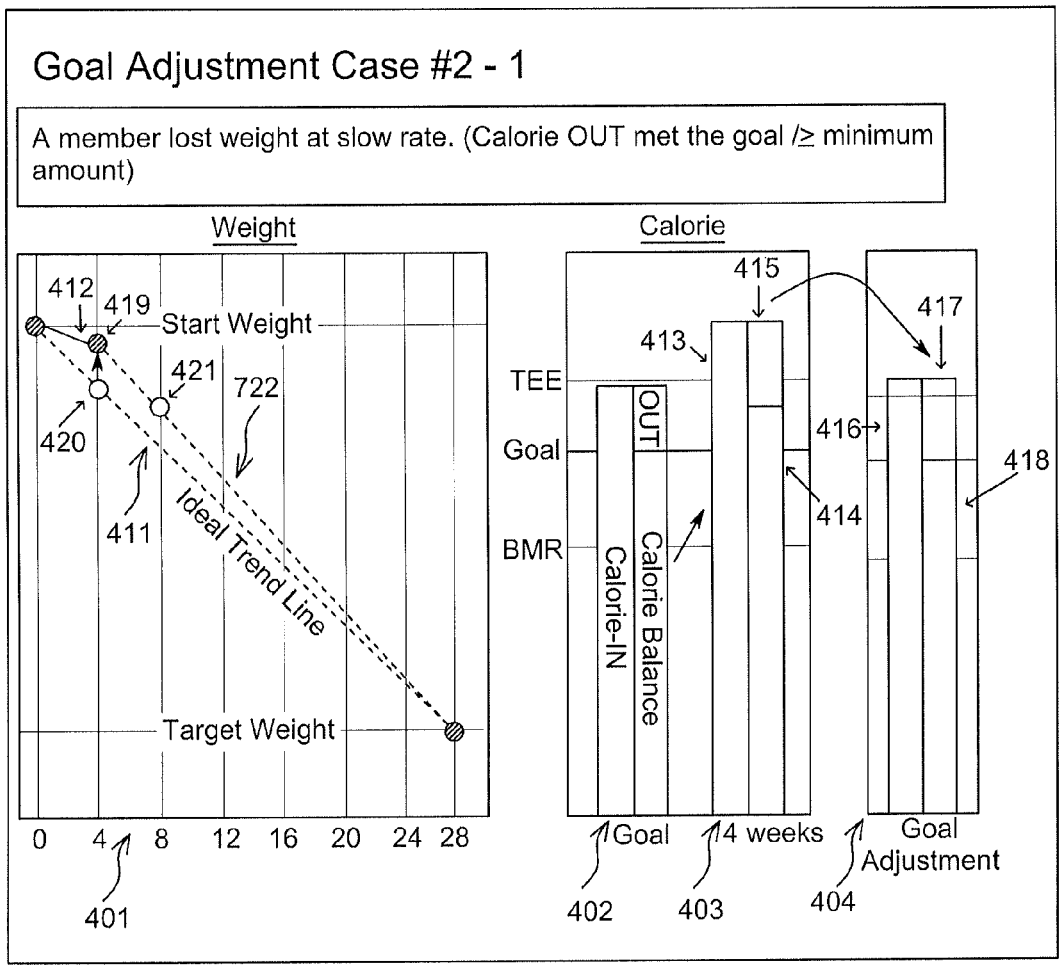
FIG. 4 provides an example of an interface which could be presented to a user of a weight management system implemented according to this disclosure.

FIG. 4 provides an example of an interface which could be presented to a user who, four weeks into a weight loss program, was losing weight, but was doing so at a rate which, if continued, would not result in the user losing 7% of his or her original body weight by the end of the weight loss program's 26 week duration. In that interface, a trend graph [401] is used to contrast an ideal weight loss trend [411] which would result in achievement of the user's weight loss goal by the end of the weight loss program with the user's actual weight loss trend [412]. To determine these trends, a weight management system [10] could be configured to start by determining the value to use for the user's weight at the time of the status update. This determination could be performed in a straightforward manner, with the system asking the user for his or her weight at the time of the status update and using the response as the user's current weight. However, it is also possible that additional analysis or calculations could be performed. For example, preferably, the user will have provided the system [10] with daily updates on his or her weight since the beginning of the weight loss program. In such a case, rather than simply treating the user's most recent update as his or her current weight, an average of multiple updates could be taken (e.g., all updates from the week preceding generation of the interface of FIG. 4, or all updates since the most recent time at which an interface such as shown in FIG. 4 was presented to the user) and treated as the user's current weight, or a trend based on multiple updates could be identified (e.g., by finding a best fit line), and then the value of that trend at the time of the status update could be treated as the user's current weight. This could have the beneficial effects of preventing the user's results from being unduly influenced by day to day variations in weight, and of allowing the system to work with a reliable weight figure even if the user might forget to enter his or her weight one or more times, or if one of more of the user's weight measurements are inaccurate. With the user's current weight determined, the actual weight loss trend [412] can be found by calculating the difference between the user's current weight and the user's initial weight, then dividing that figure by the 28 days which had elapsed since the beginning of the weight loss program. As shown, this trend [412] can be illustrated in an interface like that depicted in FIG. 4, along with data points showing the user's current weight [419] and what the user's weight would have been [420] if the user had followed the ideal weight loss trend [411].

In addition to the trend graph [401] showing the ideal [411] and actual [412] weight loss trends, the interface of FIG. 4 also includes a recommendation bar graph [402] showing the user's recommended caloric balance, recommended daily meal amount (i.e., calories in), and recommended daily exercise amount (i.e., calories out). Juxtaposed with this recommendation bar graph is an actual bar graph [403] showing the user's actual daily meal amount [413], the user's actual daily caloric balance [414], and the actual amount of exercise per day performed by the user [415]. Of these values, the user's actual daily caloric balance [414] could be determined by recalculating the user's total energy expenditure using the information provided at the inception of the weight loss program and the then current value for the user's weight, and subtracting the user's daily weight loss expressed in terms of calories. The user's actual daily exercise amount [415] and the user's actual daily meal amount [413] could be determined in a variety of manners. For example, a weight management system [10] could allow a user to input information regarding how many calories he or she consumes and how much exercise he or she performs at the end of each day, or even during the day (e.g., directly after a meal or an exercise session). With complete (presumably correct) information from the user, the user's actual daily meal amount [413] and actual daily exercise amount [414] could be determined in the same manner as described above for the user's weight. Alternatively, in the event the user provides only exercise information, it is possible that the user's actual daily meal amount [413] could be determined by adding the user's actual daily exercise amount [415] and the user's actual daily caloric balance [414]. Equivalent calculations could also be performed to determine the user's actual daily exercise amount [415] given data on the user's actual daily meal amount [413] though, as discussed in more detail in the context of FIG. 6, a weight management system implemented according to this disclosure may not be configured to perform such calculations.

Finally, the interface of FIG. 4 also provides a revised recommendation bar graph [404]. This revised recommendation bar graph [404] can reflect a revised recommended daily meal amount [416], a revised recommended daily exercise amount [417] and a revised recommended daily caloric balance [418]. These revised values can be calculated as described previously by the calorie to be reduced calculating unit [15], the caloric balance calculating unit [16] and the caloric balance setting unit [17] based on the new information provided by the user to arrive at revised values which could allow the user to achieve the desired weight loss during the pre-determined time period. That is, for a four week status update such as shown in FIG. 4, the calorie to be reduced calculating unit [15] could recalculate the weight to be lost per day by dividing the difference between the user's then current weight and the target weight determined at the initiation of the weight loss program (e.g., 241.8 lbs (109.7 kg), using the data shown in FIG. 3) by the number of days remaining in the weight loss program (i.e., 154 days, as the interface of FIG. 4 would be presented four weeks into a 26 week period) then multiplying the resulting figure by 350 to result in a revised calorie to be reduced per day amount. This new calorie to be reduced amount could be subtracted from the user's recalculated total energy expenditure to obtain the user's revised recommended daily caloric balance [418] (which, in some implementations, could be checked against, and potentially reset to, the user's updated base metabolic rate as described previously). The user's actual daily exercise amount [415] could be treated as a revised recommended daily exercise amount [417], as the user would have demonstrated an ability to perform that level of exercise. This revised recommended daily exercise amount [417] could then be added to the revised recommended daily caloric balance [418] to obtain a revised recommended daily meal amount [416]. These amounts could then be displayed in the revised recommendation bar graph [404] and a weight the user would be expected to have if he or she implemented the revised recommendations could be displayed as a data point [421] on the trend graph [401].

Figure 5:
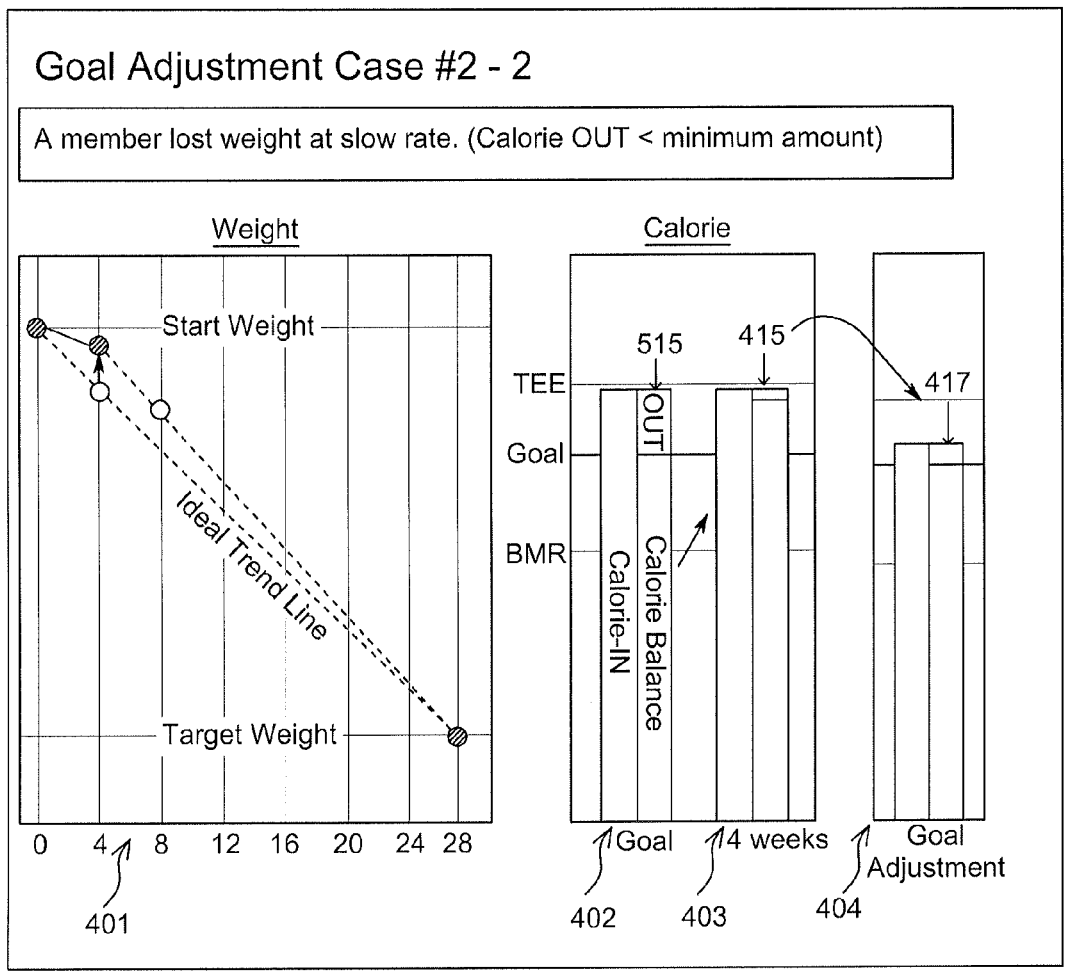
FIG. 5 provides an example of an interface which could be presented to a user of a weight management system implemented according to this disclosure.

Of course, interfaces beyond that shown in FIG. 4 could be presented to users, either based on the user's information, on the requirements for a particular implementation, or both. To illustrate, consider the interface of FIG. 5. In that interface, as in the interface of FIG. 4, the user is presented with a trend graph [401], a recommendation bar graph [402], an actual bar graph [403], and a revised recommendation bar graph [404]. However, the data shown in FIG. 5, and the relationships of the different portions of the interface representing that data, differ from what was included in FIG. 4, based on the different information for the user to whom the interface of FIG. 5 would be presented. In particular, as shown in FIG. 5, the actual daily exercise amount [415] of the user for the interface of FIG. 5 is substantially lower than the recommended daily exercise amount [515] which had been provided when the user initiated the weight loss program. Accordingly, in the interface of FIG. 5, rather than using the user's actual daily exercise amount [415] as the user's revised recommended daily exercise amount [417], the revised recommended daily exercise amount [417] is set as a minimum daily exercise amount, such as could be calculated by inserting the user's current weight into a formula like $C_{out}$=3.3 METS*weight*2.5 hours/7 days (discussed previously in the context of the caloric balance setting unit [17]). In this way, the user could be provided with a revised recommended daily exercise amount [417] which could be comfortably performed to achieve the desired weight loss within the specified time for the weight loss program.

Figure 6:
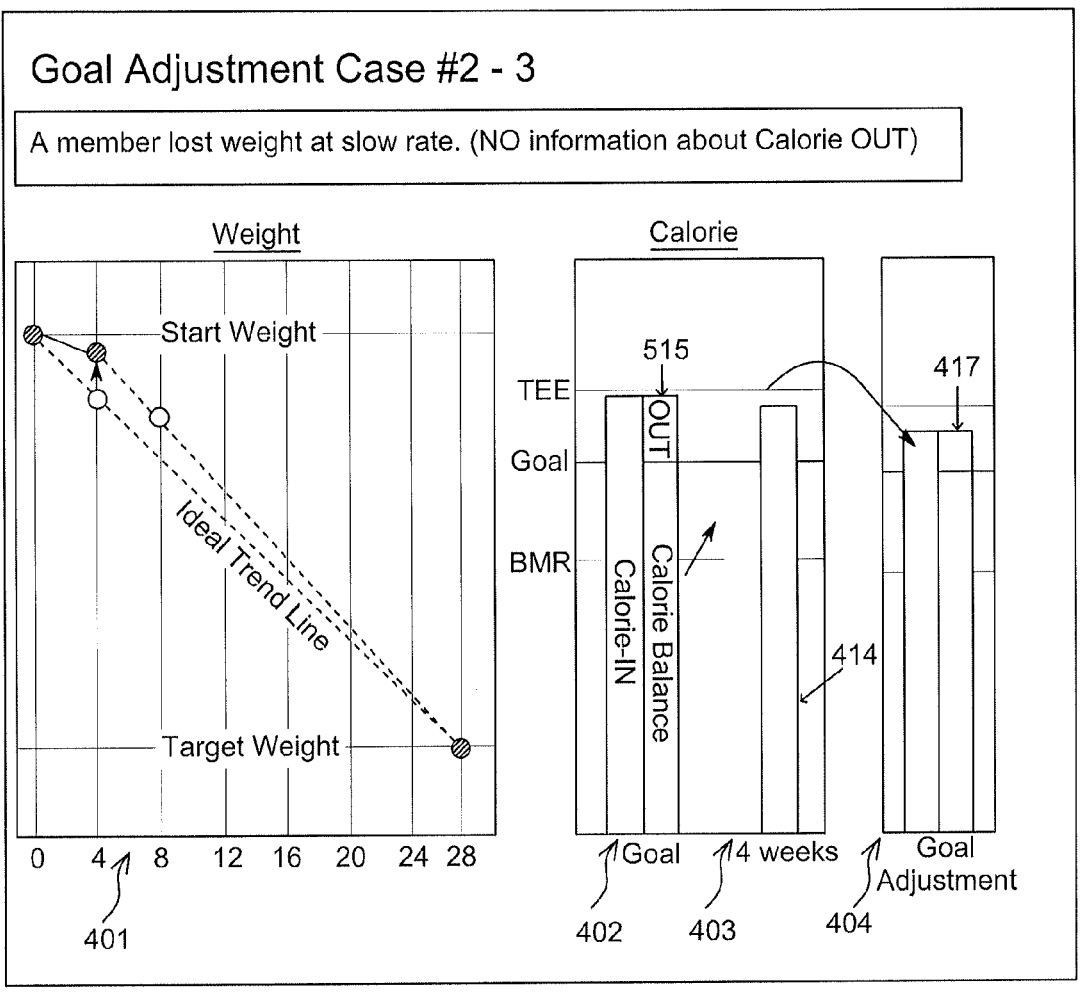
FIG. 6 provides an example of an interface which could be presented to a user of a weight management system implemented according to this disclosure.

As another example of a variation on the interfaces which could be presented to a user in a weight management system implemented according to this disclosure, consider the interface of FIG. 6. That figure illustrates one approach which can be taken by a system implemented based on this disclosure to deal with the situation where a user does not provide information which would otherwise be used in determining information which would normally be presented on an interface such as shown in FIGS. 4 and 5. In particular, the interface of FIG. 6 could be presented to a user who had not input any exercise information which would otherwise be used to determine an actual daily exercise amount. As a result of this, in the interface of FIG. 6, only the only actual daily caloric balance [414] is included in the actual bar graph [403]. As discussed in the context of FIG. 4, this value can be determined directly from the user's observed weight loss, and so would not be impacted by the failure of the user to input exercise information. However, the actual daily exercise amount and actual daily meal amount are omitted from FIG. 6, since, as discussed previously, these values will preferably be calculated based on exercise data input by the user. Similarly, in FIG. 6, rather than treating the user's actual daily exercise amount as the revised recommended exercise amount, as was described in the context of FIG. 4, the revised recommended exercise amount [417] in FIG. 6 could be determined in the same way as the user's original recommended exercise amount [515] (i.e., as described in the context of the caloric balance setting unit [17]). Of course, alternatives, such as where a user's actual daily exercise amount are determined based on meal data provided by the user, are also possible, and could be implemented by those of ordinary skill in the art without undue experimentation in light of this disclosure. However, the interface of FIG. 6 demonstrates that, while such alternatives are possible, they are not required for weight management systems implemented based on this disclosure.

Figure 7:
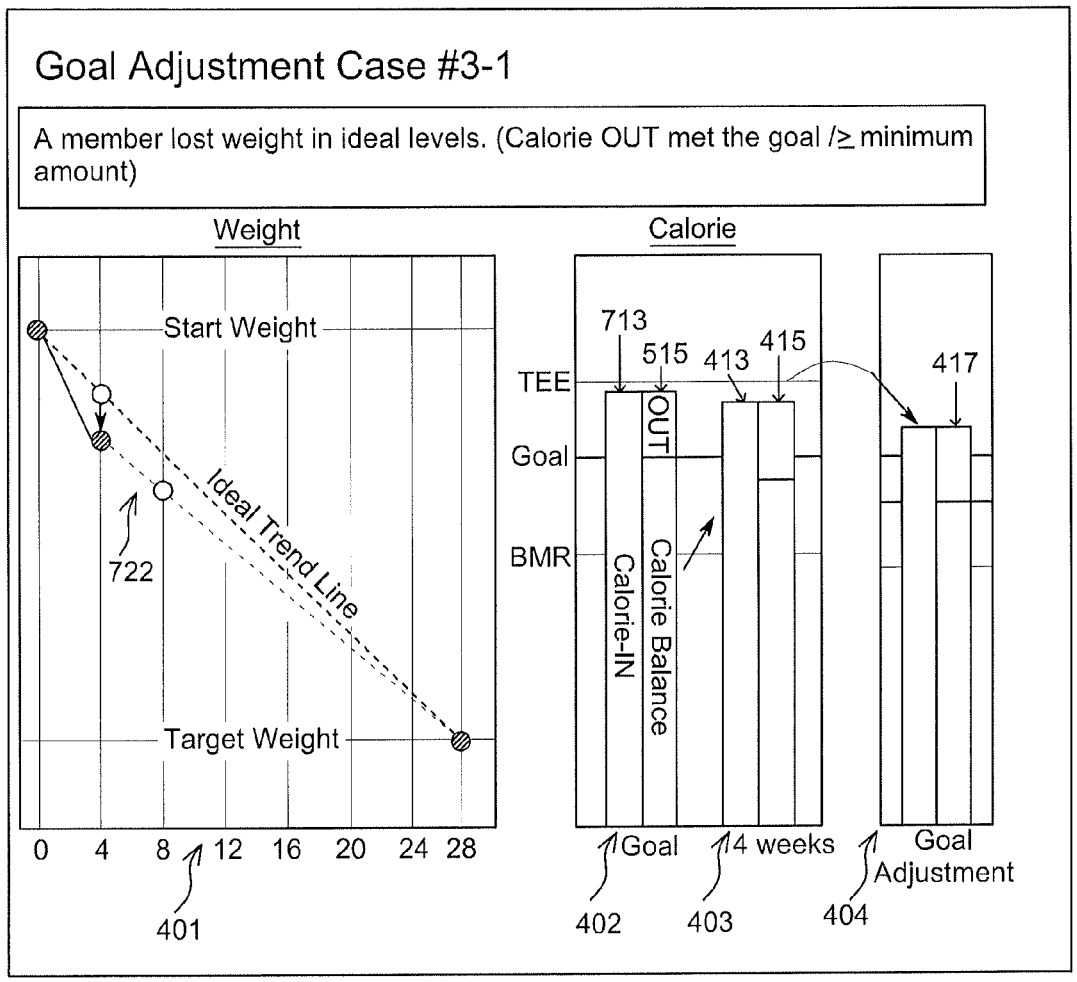
FIG. 7 provides an example of an interface which could be presented to a user of a weight management system implemented according to this disclosure.

The same techniques discussed above could also be applied to allow an information presentation unit [18] to present interfaces to users whose progression meets or exceeds what would be required to achieve the desired weight loss by the end of the weight loss program. Examples of this type of interface are provided by FIGS. 7-15. In FIG. 7, the user's actual daily exercise amount [415] exceeds the daily exercise amount which was initially recommended [515], and the user's actual daily meal amount [413] is less than the daily meal amount which was initially recommended [713]. As a result, the gradient of the future trend line [722] shown in FIG. 7 is less steep than the future trend line [722] in FIG. 4, reflecting the fact that the user for the interface of FIG. 7 would not have to lose as much weight per day to meet the goal by the end of the weight loss program as the user for the interface of FIG. 4. However, despite this difference, the calculations underlying the interface of FIG. 7 could be the same as those discussed in the context of FIG. 4, with the revised recommended exercise amount [417] being set equal to the actual daily exercise amount [415], and the revised recommended meal amount being set accordingly.

Figure 8:
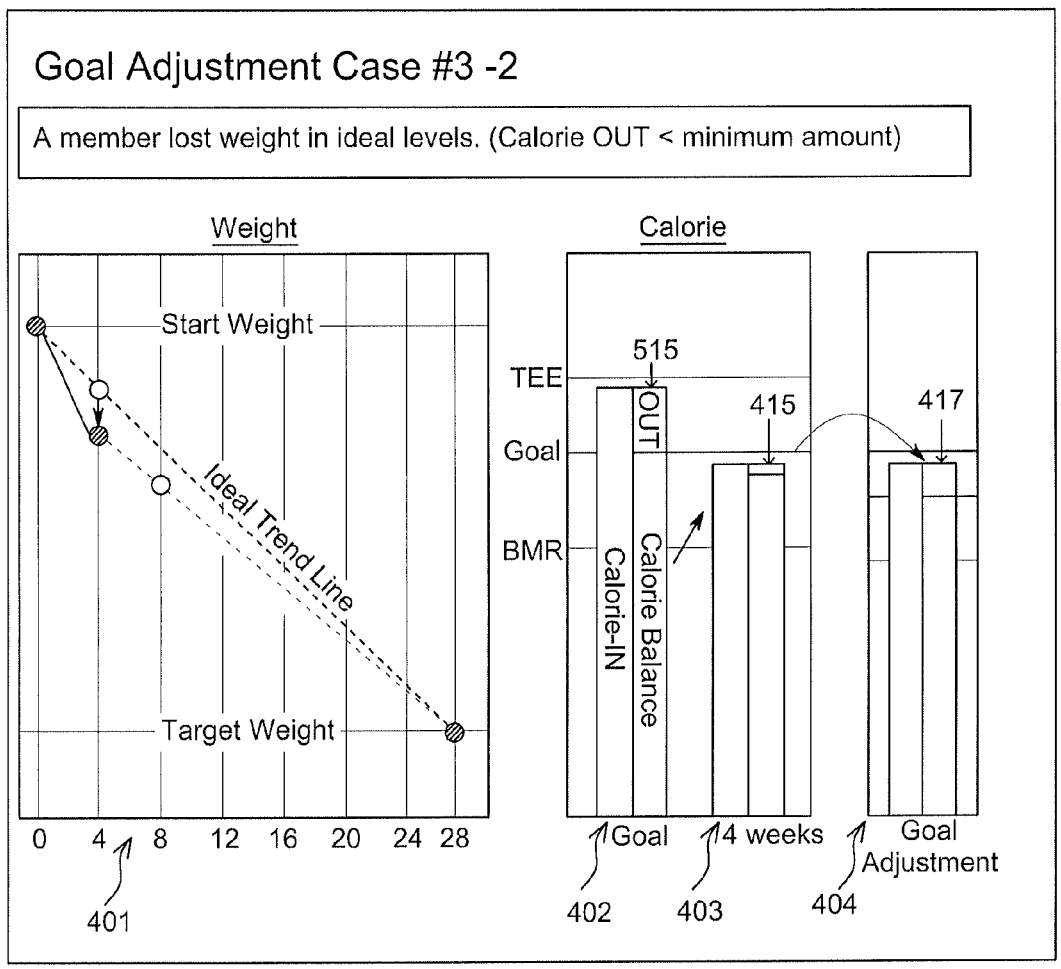
FIG. 8 provides an example of an interface which could be presented to a user of a weight management system implemented according to this disclosure.
Figure 9:
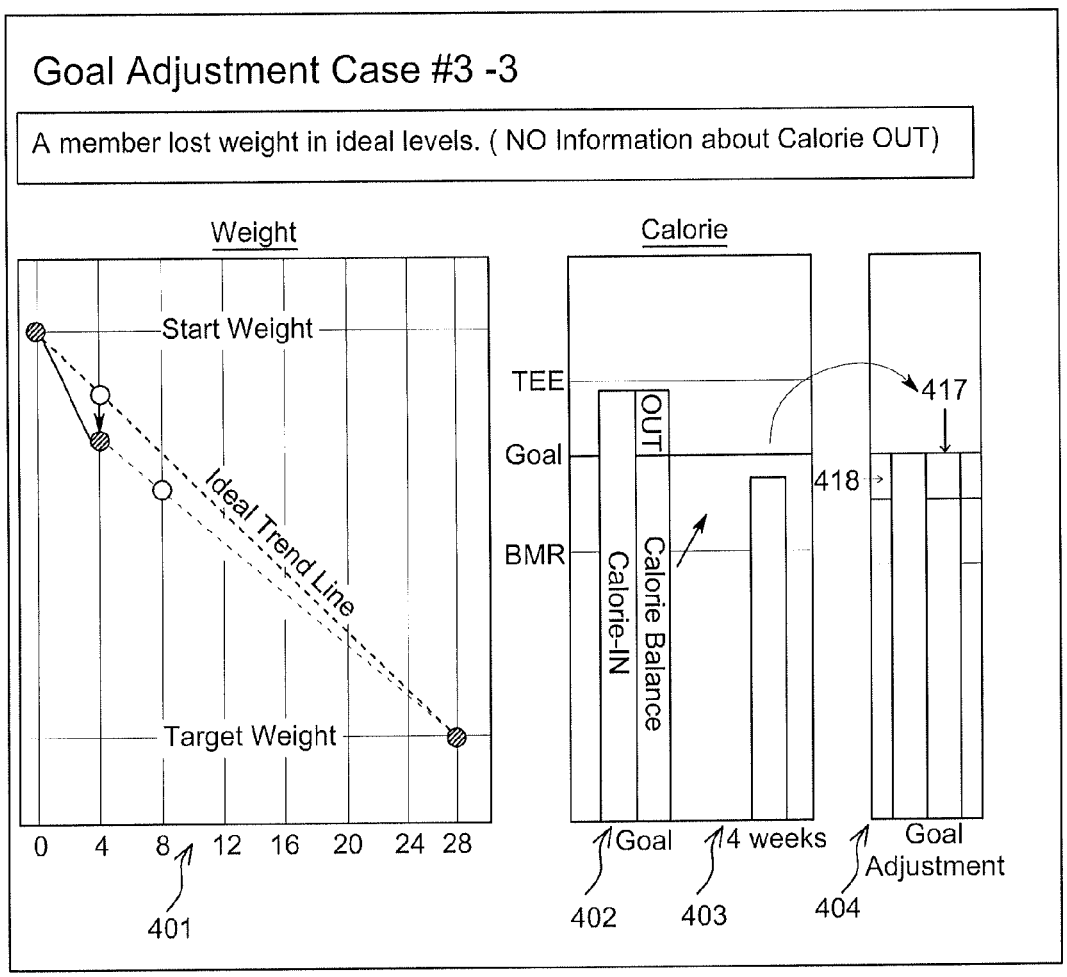
FIG. 9 provides an example of an interface which could be presented to a user of a weight management system implemented according to this disclosure.

FIGS. 8 and 9, like FIG. 7, show interfaces which could be generated using calculations which are the same as those discussed in the contexts of, respectively, FIGS. 5 and 6, though their appearance is different from the appearances of the interfaces of FIGS. 5 and 6 based on the different situations of the users corresponding to the interfaces of FIGS. 8 and 9. In particular, for both FIG. 8 and FIG. 9, the corresponding user's progress has met or exceeded what would be necessary to achieve the weight loss goal by the end of the weight loss program. However, for the user of FIG. 8, the user's actual daily exercise amount [415] has been substantially below the user's initially recommended daily exercise amount [515]. Similarly, the user of FIG. 9 has simply not provided any actual daily exercise data. As described, these users could be treated in the same way as the users of FIGS. 5 and 6. For the user of FIG. 8, as was the case with the user discussed in the context of FIG. 5, the user's revised recommended daily exercise amount [417] can be set equal to a recalculated minimum exercise amount, and the user's revised recommended daily meal amount [416] can then be recalculated accordingly. For the user of FIG. 9, as was the case with the user discussed in the context of FIG. 6, the user's actual daily exercise and meal amounts can be omitted. The user's revised recommended exercise amount [417] can then be set using the same techniques discussed in the context of the caloric balance setting unit [17], and the user's revised recommended daily meal amount [416] can then be recalculated accordingly.

Figure 10:
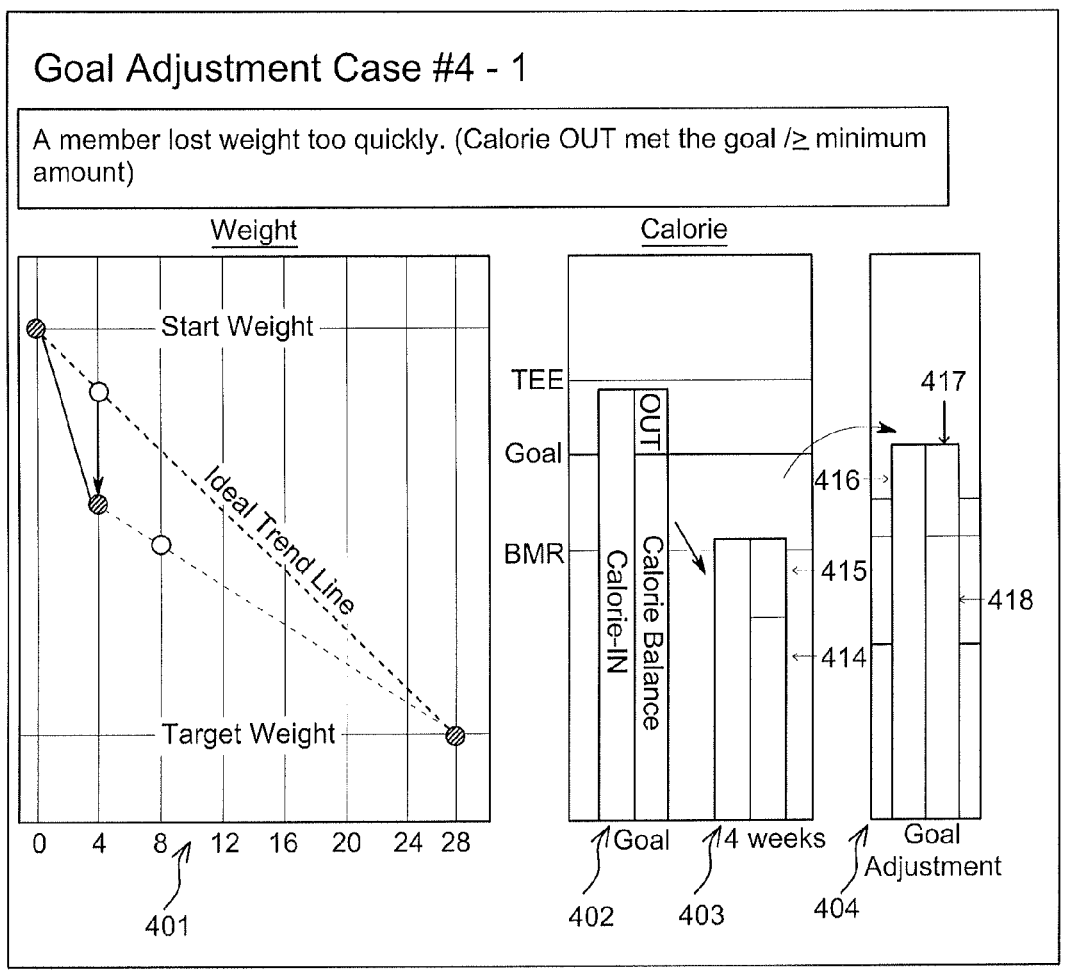
FIG. 10 provides an example of an interface which could be presented to a user of a weight management system implemented according to this disclosure.
Figure 11:
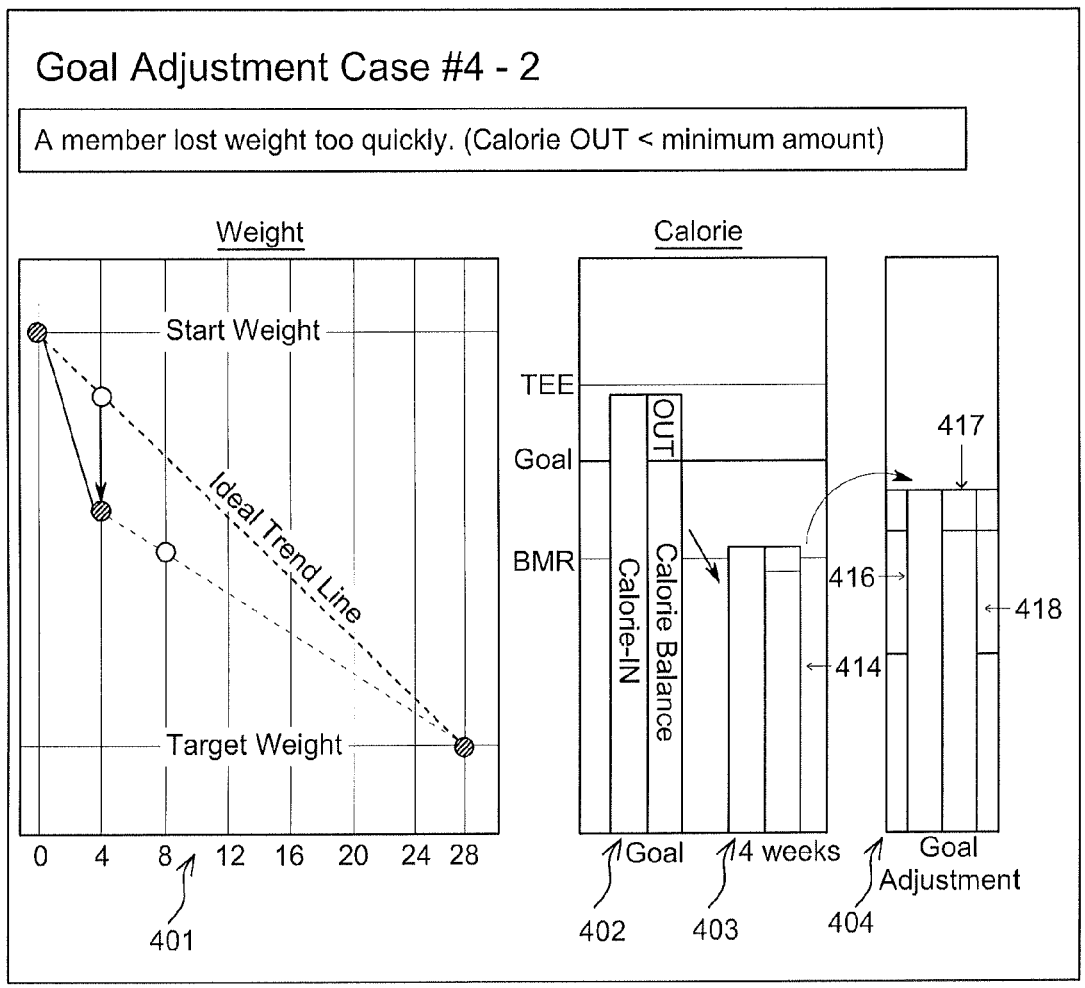
FIG. 11 provides an example of an interface which could be presented to a user of a weight management system implemented according to this disclosure.
Figure 12:
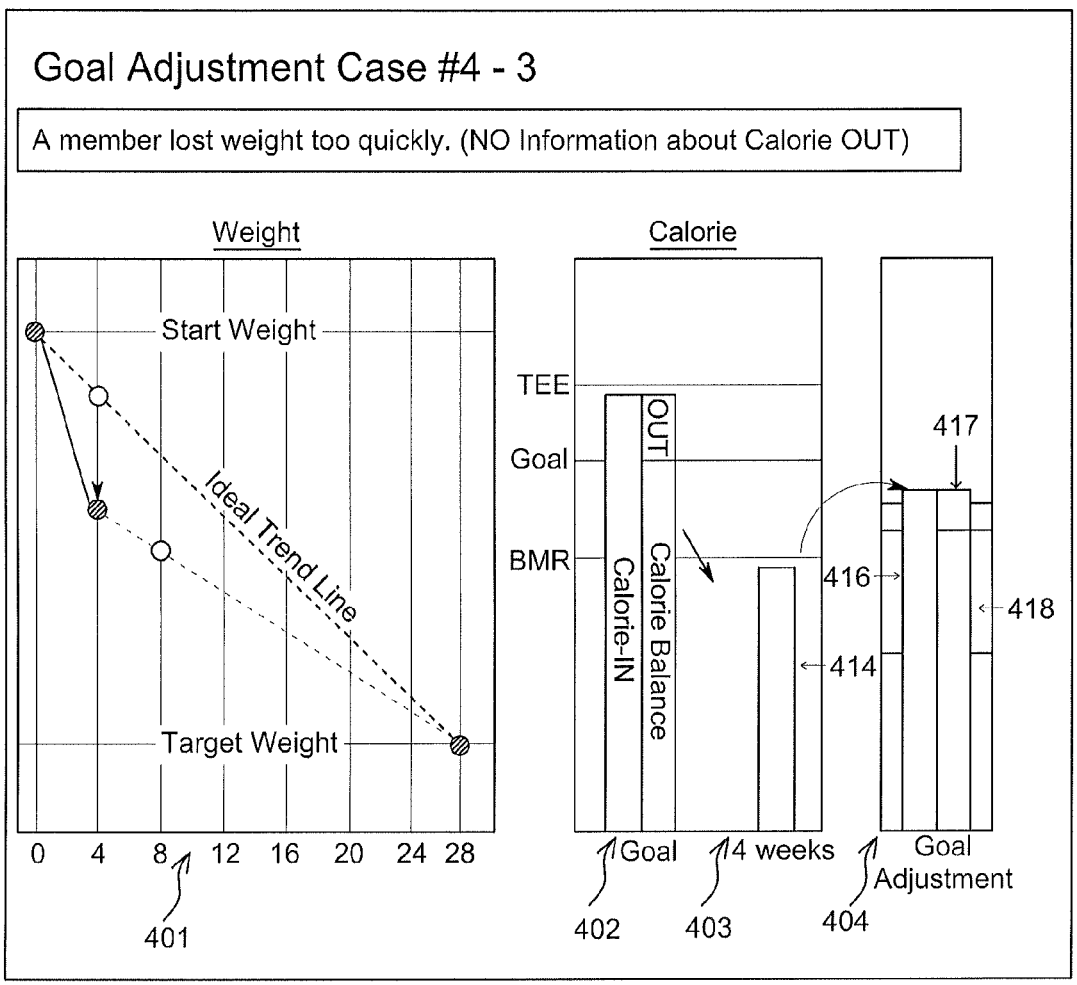
FIG. 12 provides an example of an interface which could be presented to a user of a weight management system implemented according to this disclosure.

FIGS. 10-12 also depict interfaces which could be presented to users who have made progress which meets or exceeds what would be necessary to achieve the weight loss goal by the end of the weight loss program. However, the users associated with these interfaces have lost weight at a rate substantially greater than that associated with FIGS. 7-9. In particular, these users have lost weight a rate which indicates that their actual caloric balance [414] is below their base metabolic rate, which is a minimum level which should be met by all users.

Despite this difference, the calculations performed for the users associated with FIGS. 10-12 can be the same as the calculations discussed previously in the context of FIGS. 7-9. That is, for FIG. 10, the user's revised recommended exercise amount [417] is set equal to the user's daily actual exercise amount [415] and the user's revised recommended meal amount [416] is recalculated accordingly as the sum of the user's revised recommended caloric balance [418] and the user's revised recommended caloric balance [418]. For FIG. 11, the user's revised recommended exercise amount [417] is reset as a minimum daily exercise amount calculated as described previously in the context of the calorie balance setting unit [17], and the revised recommended meal amount [416] is recalculated as the sum of the user's revised recommended caloric balance [418] and the user's revised recommended daily exercise amount [417]. Finally, for FIG. 12, as no exercise information was provided by the user associated with that figure, that figure omits the user's actual daily exercise amount and actual daily meal amount, and sets the user's revised recommended daily exercise amount [417] using techniques such as discussed previously in the context of the initial determination of the recommended daily exercise amount by the caloric balance setting unit [17]. Then, as was the case with FIGS. 10 and 11, once that value has been determined, it can be used in calculating a revised recommended daily meal amount [416], by adding the revised recommended daily exercise amount [417] with the user's revised recommended caloric balance [418], which had been recalculated based on the health information provided by the user at the inception of the weight loss program, the user's then current weight, and the time remaining in the weight loss program.

Figure 13:
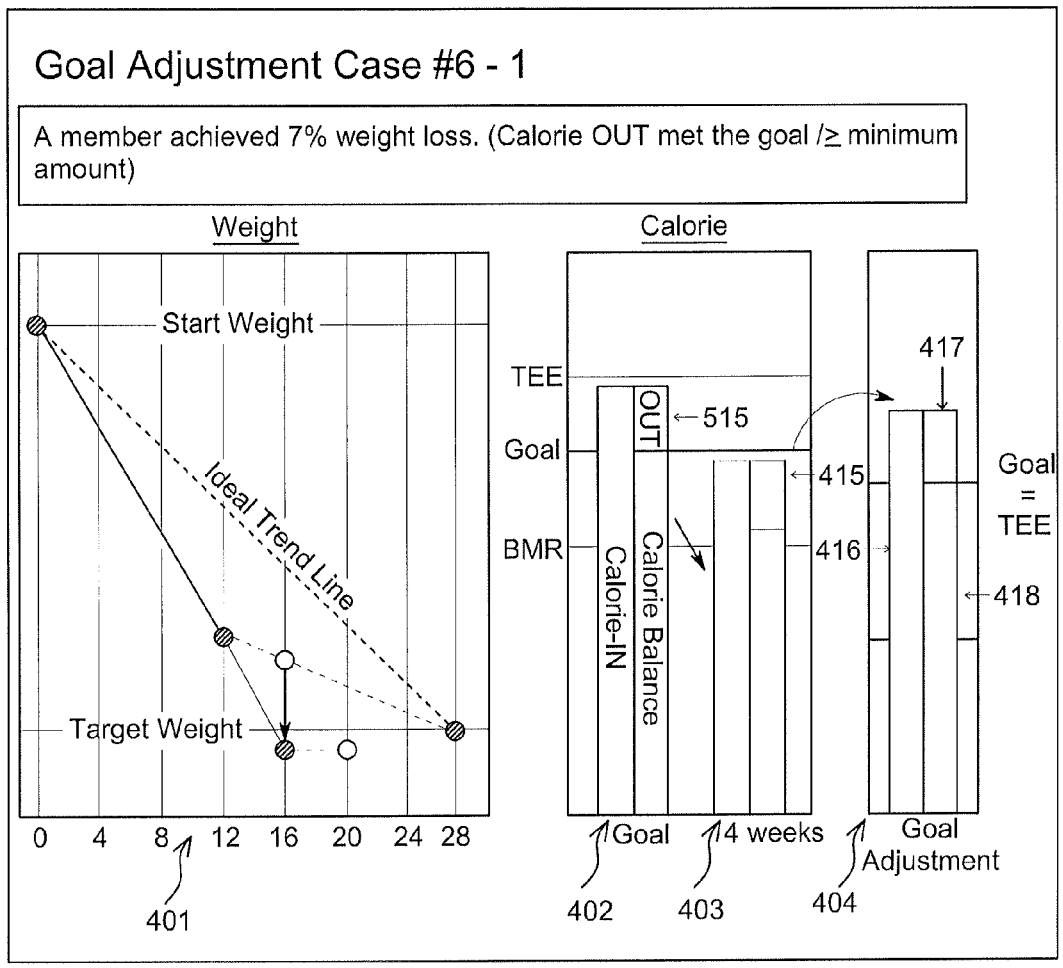
FIG. 13 provides an example of an interface which could be presented to a user of a weight management system implemented according to this disclosure.
Figure 14:
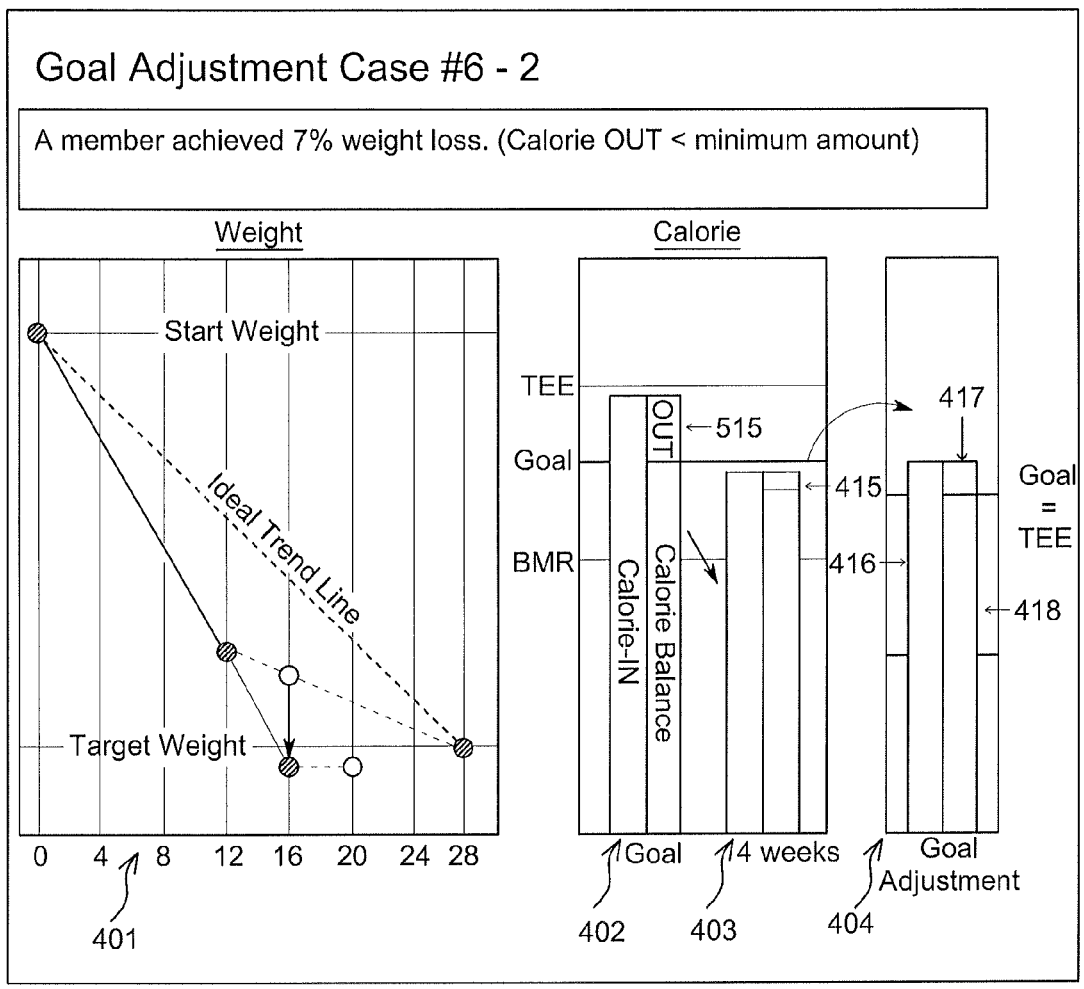
FIG. 14 provides an example of an interface which could be presented to a user of a weight management system implemented according to this disclosure.
Figure 15:
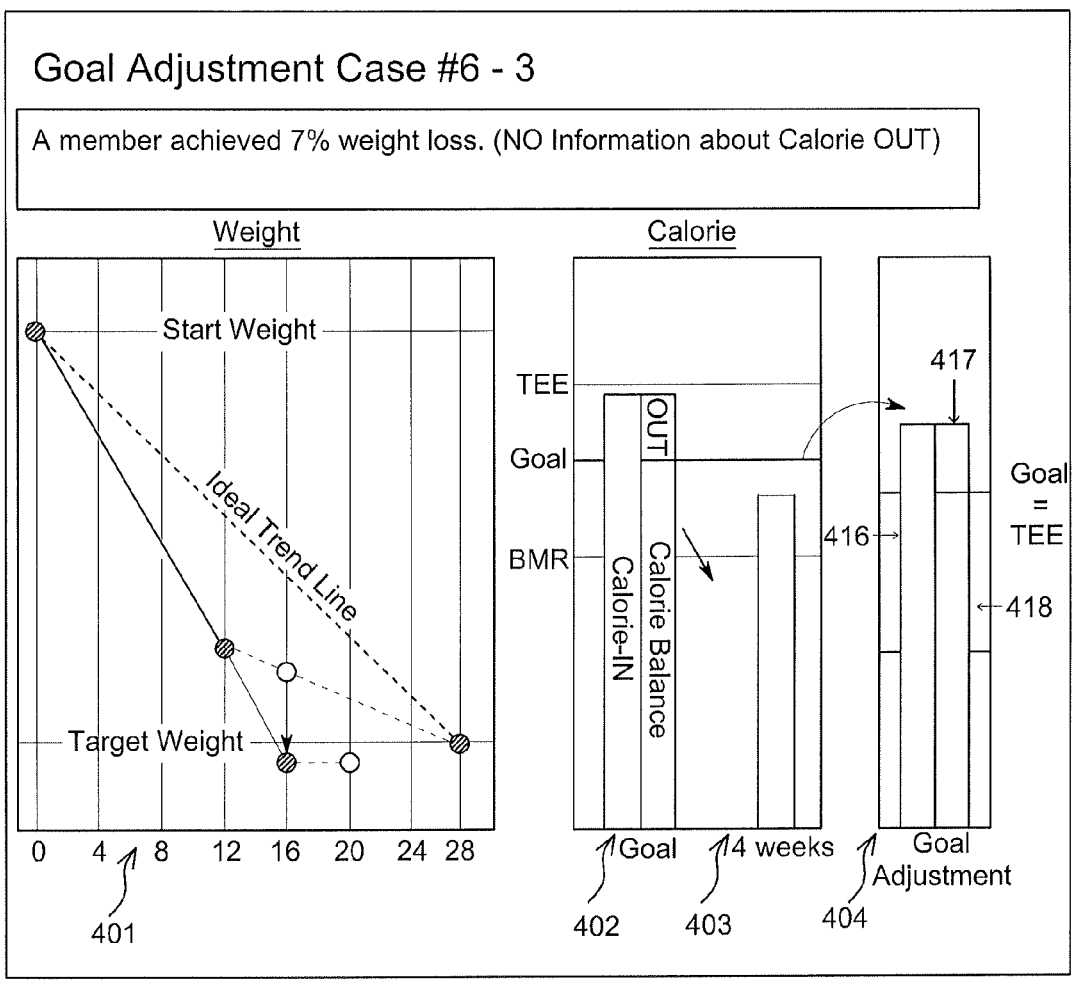
FIG. 15 provides an example of an interface which could be presented to a user of a weight management system implemented according to this disclosure.

Of course, not all interfaces presented by an information presentation unit [18] in a weight management system [10] implemented according to this disclosure will necessarily be supported by the same calculations described above in the context of FIGS. 4-12. To illustrate, consider FIGS. 13-15, which could be presented to users whose progress has been rapid enough that those users have achieved the target weight loss prior to the predetermined completion of the weight loss program. Because the users to whom those interfaces would be presented had met their weight loss target, the information included in the revised recommendation bar graphs [404] of FIGS. 13-15 is based on assisting the users to maintain their then current weight, rather than providing recommendations which would, if followed, be expected to result in further weight loss. Accordingly, in FIGS. 13-15, rather than being determined based on the difference between the user's then current weight and the target weight, and the amount of time left in the weight loss program, the revised recommended caloric balances [418] of FIGS. 13-15 are simply set equal to the user's total energy expenditure, which is recalculated based on the user's then current weight and the information provided at the initiation of the weight loss program. The revised recommended daily exercise amounts [417] are then set using the same techniques as discussed previously. That is, if the user's actual daily exercise amount [415] was greater than or equal to his or her recommended daily exercise amount [515] (as illustrated in FIG. 13), the user's revised recommended daily exercise amount [417] would be set equal to his or her actual daily exercise amount [415]. If the user's actual daily exercise amount [415] is less than his or her recommended daily exercise amount [515] (as illustrated in FIG. 14), the user's revised recommended daily exercise amount [417] could be set equal to the minimum daily exercise amount determined based on the user's then current weight using techniques such as discussed previously in the context of the caloric balance setting unit [17]. If the user had simply not provided information on his or her actual daily exercise amount (as illustrated in FIG. 15), the user's revised recommended daily exercise amount [417] could be determined using techniques such as discussed previously in the context of the initial determination of the recommended daily exercise amount by the caloric balance setting unit [17]. Then, for each of FIGS. 13-15, once the revised recommended daily exercise amount [417] had been determined, it could be added to the revised recommended daily caloric balance [418] to determine the user's revised recommended daily meal amount [416].

Interfaces which could be presented to a user by an information presentation unit [18] are also not limited to including only the information described with respect to FIGS. 4-15. Instead, depending on the context and the requirements for a particular implementation, interfaces could also be generated to provide the user with additional information and/or functionality. As an example of this, consider the interface of FIG. 16, which could be presented to a user whose weight had increased since the inception of a weight loss program. The interface of FIG. 16, rather than providing a single revised recommendation bar graph, presents the user with a first alternative revised recommendation bar graph [1604] and a second alternative revised recommendation bar graph [1605]. These alternative recommendation bar graphs [1604][1605] can be used in cases where there might be multiple possible approaches to setting a goal for a user. For example, a user can be given choices between picking a recommendation which would help him or her reach an interim weight loss goal before the completion of the weight loss program, a recommendation which would help him or her reach an ultimate weight loss goal by the end of the weight loss program, and recommendations which would allow users to reach interim or ultimate weight loss goals in a non-linear manner (e.g., recommendations which gradually ease a user into exercising or controlling calorie intake).

What choices are presented in any particular situation can be based on a number of factors. For example, if a particular weight management system [10] is not configured with calculations to support a particular type of recommendation (e.g., if it does not include formulas which could calculate non-linear weight loss progressions), then that that type of recommendation would not be presented to the user. Similarly, if a particular type of recommendation is not consistent with a user's current situation, then it may also not be presented, even if the weight management system [10] is configured to perform the relevant calculations. For example, before presenting a recommendation which includes an interim goal, a weight management system [10] could check if reaching that interim goal was consistent with achieving the ultimate objective of the user losing 7% of his or her original body weight by the end of the weight loss program. If it was not (e.g., if the weight loss which would be necessary after reaching the interim goal was so drastic that it would require a daily caloric balance which was less than the user's base metabolic rate) then the user might not be presented with the recommendation which includes that interim goal.

Figure 16:
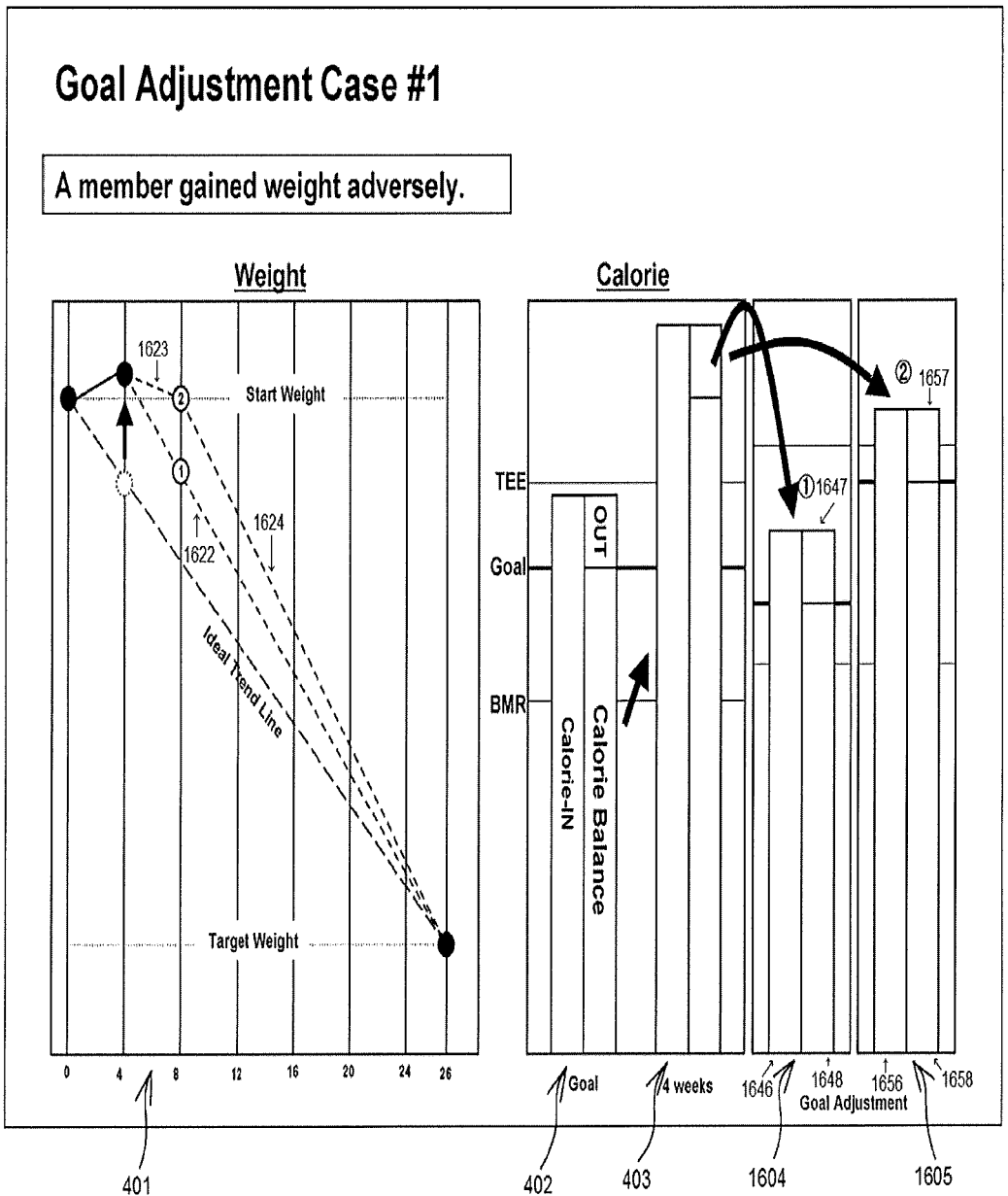
FIG. 16 provides an example of an interface which could be presented to a user of a weight management system implemented according to this disclosure.

As a concrete example of how alternative recommendation bar graphs [1604][1605] can be determined, consider the calculations which could underlie the alternative recommendation bar graphs [1604][1605] of FIG. 16. In FIG. 16, the first alternative recommendation bar graph [1604] presents a user with potential recommended daily amounts for exercise [1647], caloric balance [1648], and food [1646] which would be consistent with the user achieving the desired weight loss by the conclusion of the weight loss program. The second alternative recommendation bar graph [1605], presents a user with alternative potential daily amounts for exercise [1657], caloric balance [1658], and food [1656] which would be consistent with the user losing the weight gained since the previous status update (e.g., the weight gained since the status update four weeks prior to the recommendation being presented, which, in the case of FIG. 16, would be the weight gained since the start of the weight loss program) by the time of the next scheduled status update (e.g., four weeks hence). These alternative recommendation bar graphs [1604][1605] can be accompanied by additional information in the trend graph [401], showing the rate of progress which would be required for the user to achieve the target weight loss by the end of the weight loss program using the first set of recommendations [1622], and the rates of progress which would be required under the second set of recommendations, both for the user to return to his or her starting weight [1623] and to achieve the target weight loss before the end of the weight loss program thereafter [1624]. With this information (or other information, as might be provided in a particular implementation), the user can choose between different ways of proceeding with the weight loss program, that choice can be stored in the user information database [101], and then used subsequently for evaluating the user's progress toward reaching the weight loss goal.

In addition to the information presentation unit [18], group determining unit [19], caloric balance setting unit [16], and other components discussed above, a weight management system [10] implemented using the disclosed technology could also include other components, such as a meal menu presentation unit [21]. Such a meal menu presentation unit [21] could be used, for example, to determine foods which a user could select consistent with the recommended daily meal amounts provided by the weight management system [10]. For example, a meal menu presentation unit [21] could interact with a meal menu storing unit [212] to retrieve menus of potential meals for the user from a meal menu database [102] and present those menus of meals to the user so that he or she could choose from a variety of options consistent with his or her recommended daily meal amount. A meal menu presentation unit [21] could also present the user with personalized meal plans (e.g., collections of multiple meals, such as breakfast, lunch and dinner to be eaten in a single day) from which the user could choose. Also, depending on the implementation, some or all of the meals (whether included in a menu or a meal plan) could be accompanied by recipes, so that the user himself or herself could prepare the meals if desired.

Concretely, this meal presentation functionality could be supported by providing an interface on an administrator terminal [131] which could allow the administrator to input data regarding various types of meals (optionally including recipes for those meals) that would be offered to the user as a meal recommendation, along with calorie information for each of those meal options. These could then be organized into various types of meal menus (e.g., breakfast, lunch and dinner menus), and classified according to their caloric content (e.g., menus of meals having 1,200 calories, menus of meals having 1,500 calories, menus of meals having 1,800 calories, menus of meals having 2,000 calories, menus of meals having 2,400 calories, etc) and/or personalized for a user based on a determined user recommended meal amount that is a recommendation of a daily amount of calories to consume. Menus could also be provided for food items which could be eaten between meals, for example there could be a menu of food items having between 100 and 200 calories which could be eaten as snacks. The meal menu presentation unit [21] could then retrieve the appropriate menus of meals based on the user's recommended daily meal amount and present the retrieved menus to the user as an aid to assisting the user in reaching his or her weight loss goal.

Of course, it is also possible that, rather than allowing user to select from a menu of meals or meal plans, a weight management system [10] implemented according to this disclosure could be configured to simply assign meals or meal plans to the user. It is also possible that a combined approach could be taken, such as where a portion of a user's calorie intake could be accounted for by a meal or meal plan assigned to the user, and the user allowed to choose from a menu of options to account for his or her remaining calorie intake. Other variations, such as systems where users are allowed to choose whether a meal or meal plan will be assigned (e.g., if a user has difficulty deciding and wants the weight management system [10] to make the decision) are also possible, and could be implemented by one of ordinary skill in the art without undue experimentation based on this disclosure. Accordingly, the above description should be understood as being illustrative only, and should not be treated as limiting.

Just as a weight management system [10] implemented according to this disclosure can include components and features which would allow a user to be presented with a selection of meals, so such a weight management system could be implemented to allow a user to be presented with a selection of exercises. In particular, a weight management system could be implemented to include an exercise menu presentation unit [22] which could interact with an exercise menu storing unit [222] and an exercise menu database [103] to present exercise menus in the same way as described above in the context of using a meal menu presentation unit [21], meal menu storing unit [212] and meal menu database [102] to present the user with menus of potential meals. Further, an exercise menu presentation unit [22] could also include functionality to not only present the user with a menu of potential exercises, but could also present the user with information on how long those exercises would need to be performed in order for the user to meet his or her daily recommended exercise amount. Similarly, as with the meal menu presentation unit [21], and exercise menu presentation unit [22] could be configured to present different plans of exercise (e.g., combinations of activities the user could engage in), rather than only presenting individual exercises for the user. Accordingly, like the discussion of the meal menu presentation unit [21], the description of the exercise menu presentation unit [22] set forth above should be understood as being illustrative only, and should not be treated as limiting.

It should be understood that, while the above disclosure explained and illustrated the inventors' technology using examples of a weight management system using a particular architecture and particular components to assist individuals who had or were at risk of developing diabetes to lose a predetermined amount of weight (7% of the user's initial body weight) within a predetermined time period (26 weeks), the inventor's technology is not limited to being implemented using the precise components and architecture, or in the precise context, described above. For example, the inventors' technology could also be used to assist individuals who do not have, and are not at risk of developing, diabetes to achieve their goals with respect to their weight, which goals could include weight loss, weight maintenance, or even weight gain. Similarly, while the discussion above focused on assisting a user to lose a predetermined amount of weight in a predetermined time period, it is possible that a user might be able to set his or her own weight goals, and his or her own time period for achieving those goals.

In addition to variations on the target users, it is also possible that different implementations will vary according to whether they treat users individually or as groups. For example, it is possible that a corporate wellness program could use the inventors' technology to support weight loss by participants in the program (e.g., by adding information on food in the company cafeteria and surrounding restaurants to the meal menu database, by adding information on exercises which could be performed at the company gym or which could be performed by signing up for a company sports team to the exercise menu database, etc.) by providing each individual participant with their own weight loss goal and period. However, it is also possible that a corporate wellness program could try and encourage participants to lose additional weight by combining them into teams (e.g., by departments in the company) and modifying the information presented to the users to show how their particular weight progress contributes to the progress of their team.

Variations are also possible in the architecture or organization of components which could be used when implementing the inventors' technology. For example rather than having separate classes of user and administrator terminals, the inventors' technology could be used to implement a weight management system which was open to the public (e.g., an internet weight loss tool) and which would have users enter their own information about preferred exercises and menus, rather than requiring this information to be input by a separate administrator terminal. Other variations on the architecture of FIG. 1 are also possible (e.g., the information for the various databases shown in FIG. 1 could be stored on a single physical machine, rather than in separate machines as shown).

Variations are also possible in the implementation and organization of the different modules described in the context of the management server [11] of FIG. 2. While each of the functional units illustrated for the management server [11] in FIG. 2 will preferably be implemented by a different module or application executing on a server computer, one or more of those functional units could be combined (e.g., as separate methods of a single application), or hosted by a device other than a management server as shown. For example, the disclosed technology could be embodied in a downloadable application, in which case the functional units would operate on the user's local device, or it could be provided by a cloud based service, in which case the functional units would likely be spread across multiple physical devices for purposes such as load balancing and redundancy purposes.

Similarly, functionality described above as being supported by different modules could be combined in some weight management systems [10] implemented according to this disclosure. For example, while the calorie to be reduced calculating unit [15] and caloric balance calculating unit [16] were described previously as separate components, in some implementations, those components could be combined into a single component which calculates the amount of calories to be reduced, the user's metabolic rate and total energy expenditure, and recommended caloric balance. Such a component could then perform its calculations in the same manner as described for the calorie to be reduced calculating unit [15] and caloric balance calculating unit [16], but it could also approach those calculations in a different manner. For example, a component which determined the calorie reduction amount, the base metabolic rate and the total energy expenditure could check if the calorie reduction amount was greater than the difference between the user's total energy expenditure and his or her base metabolic rate (e.g., by checking if the calorie reduction amount was more than 30% of the user's base metabolic rate, in implementations where the total energy expenditure is determined by multiplying the base metabolic rate by 1.3). Then, if the calorie reduction amount was greater than the difference between the total energy expenditure and the base metabolic rate, the calorie reduction amount could be set equal to the difference between the user's total energy expenditure and base metabolic rate, and the revised calorie reduction amount could then be used to calculate the user's recommended caloric balance, and for other purposes as might be appropriate in that implementation.

Other variations are also possible, and will be immediately apparent to those of ordinary skill in the art in light of this disclosure. Accordingly, instead of limiting the protection accorded by this document, or by any document which is related to this document, to the material explicitly disclosed herein, the protection should be understood to be defined by the following claims, which are drafted to reflect the scope of protection sought by the inventors in this document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to the claims based on the above disclosure or the incorporated priority documents is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

Explicit Definitions

When used in the claims, "based on" should be understood to mean that something is determined at least in part by the thing that it is indicated as being "based on." When something is completely determined by a thing, it will be described as being "based EXCLUSIVELY on" the thing.

When used in the claims, "comprises" should be understood to mean includes, but is not limited to. For example, the months of the year could be described as "comprising" January, July, and October. Similarly, a statement that something is "comprised by" some entity should be understood to mean that the entity comprises the thing it is described as "comprised by". For example, January, July and October could be described as "comprised by" the months of the year. It should be understood that the "comprises" relationship is transitive. For example, the statements that the months of the year "comprise" the months of spring, and that the months of spring "comprise" April, necessarily imply that the months of the year comprise April. The statements that April is "comprised by" the months of spring, and that the months of spring are "comprised by" the months of the year, necessarily imply that April is "comprised by" the months of the year.

When used in the claims, "computer" should be understood to refer to a device, or group of devices, which is capable of performing one or more logical and/or physical operations on data to produce a result. Non-limiting examples of "computers" include multiprocessor or multicore systems, servers, laptops, desktops, netbooks, and notebooks, as well as handheld devices such as smart phones, personal digital assistants, and portable game consoles. In the claims, certain adjectives may be used with the term "computer" and should be understood to be included for the purposes of readability (e.g., by avoiding ambiguity in antecedent basis). For example, "terminal computer", "server" and "server computer" should be understood as being synonymous with each other, and should not be treated as implying limitations on the types of "computers" referred to in the claims (e.g., a "terminal computer" could be a smart phone).

When used in the claims, "configured" should be understood to mean that the thing "configured" is adapted, designed or modified for a specific purpose. An example of "configuring" in the context of computers is to provide a computer with specific data (which may include instructions) which can be used in performing the specific acts the computer is being "configured" to do. For example, installing Microsoft WORD on a computer "configures" that computer to function as a word processor, which it does by using the instructions for Microsoft WORD in combination with other inputs, such as an operating system, and various peripherals (e.g., a keyboard, monitor, etc).

When used in the claims, to "determine" something should be understood to refer to the act of generating, selecting or otherwise specifying the thing "determined". For example, to obtain an output as the result of analysis would be an example of "determining" that output. As a second example, to choose a response from a list of possible responses would be a method of "determining" a response.

When used in the claims, the verb "display" refers to the act of providing the thing "displayed" in a visually perceptible form. It should be understood that, in the context of this disclosure, "displaying" refers not only to actually physically presenting a thing on a screen, but also to causing that thing to be presented (e.g., by sending instructions from a local CPU, or by sending information over a network which causes a thing to be "displayed").

When used in the claims, a statement that some data, such as a file, is "local" to a computer should be understood to mean that the computer can access the data without using a wide area network or sneakernet.

When used in the claims, the phrase "means for determining a user segment" should be understood as a means+function limitation as provided for in 35 U.S.C. §112 ¶ 6, in which the function is "determining a user segment" and the corresponding structure is a computer configured to perform processing such as described in the context of the group determining unit [19].

When used in the claims, the phase "means for determining a user recommended exercise amount" should be understood as a means+function limitation as provided for in 35 U.S.C. §112 ¶ 6, in which the function is "determining a user recommended exercise amount" and the corresponding structure is a computer configured to perform processing such as described in the context of the caloric balance setting unit [17].

When used in the claims, "non-transitory computer readable medium" should be understood to refer to any object, substance, or combination of objects or substances, capable of storing data or instructions in a form in which they can be retrieved and/or processed by a computer. Computer memory such as hard discs, read only memory, random access memory, solid state memory elements, optical discs and registers are examples of "non-transitory computer readable media." However, for the avoidance of doubt "non-transitory computer readable media" should not be understood as including ephemeral transmissions, such as propagating signals.

When used in the claims, the term "set" should be understood to refer to a number, group, or combination of zero or more things. When something is determined based on a "set", it should be understood to mean that the determination is based on one or more of, but not necessarily all of, the things from the "set". For example, a statement that something is determined based on an updated set of health data should be understood as being synonymous with a statement that something is determined based on data from the updated set of health data.

Regarding the above mentioned embodiments, the present invention also includes other embodiments described below, related to the method, the non-transitory computer readable medium, and machine.

<1> A method comprising:
a. at a server, receiving an initial set of health data for a user and a set of segmentation data for the user;
b. calculating a minimum exercise amount based on the initial set of health data for the user;
c. determining a user segment based on the set of segmentation data for the user;
d. determining a user recommended exercise amount based on applying an exercise modification factor to the minimum exercise amount, wherein the exercise modification factor corresponds to the user segment;
e. storing the user recommended exercise amount in a database communicatively connected to the server; and
f. displaying, via a terminal computer, a user exercise recommendation based on the user recommended exercise amount.

<2> The method of <1>, further comprising:
a. determining, based on the initial set of health data for the user, a user total energy expenditure and a user calorie reduction amount;
b. setting a user recommended caloric balance equal to the user total energy expenditure minus the user calorie reduction amount;
c. determining a user recommended meal amount based on adding the user recommended exercise amount to the user recommended caloric balance;
d. storing the user recommended meal amount in the database; and
e. displaying a user meal recommendation based on the user recommended meal amount.

<3> The method of <1> or <2>, further comprising:
a. receiving an updated set of health data for the user;
b. determining, based on the updated set of health data for the user, an updated user total energy expenditure and an updated user calorie reduction amount;
c. setting an updated user recommended caloric balance equal to the updated user total energy expenditure minus the updated user calorie reduction amount;
d. determining an updated user recommended exercise amount based on the updated set of health data for the user;
e. determining an updated user recommended meal amount based on adding the updated user recommended exercise amount to the updated user recommended caloric balance;
f. storing the updated user recommended meal amount and the updated user recommended exercise amount in the database;
g. displaying an updated user meal recommendation based on the updated user recommended meal amount and an updated user exercise recommendation based on the updated user recommended exercise amount; and
h. repeating steps a-g one or more times during a weight management program.

<4> The method of <1> to <3>, wherein determining, based on the updated set of health data for the user, the updated user total energy expenditure and the updated user calorie reduction amount comprises:
a. determining the updated user total energy expenditure by applying an enhancement to a user metabolic rate determined based on:

i. a weight from the updated set of health data for the user;
ii. a height from the initial set of health data for the user;
iii. an age for the user; and
iv. a gender from the initial set of health data for the user;
b. setting a remaining amount to lose based on a difference between:
   i. a target weight determined at the inception of the weight management program based on the initial set of health data; and
   ii. the weight from the updated set of health data for the user; and
c. determining the updated user calorie reduction amount based on:
   i. a result of dividing the remaining amount to lose by a remaining duration of the weight management program; and
   ii. comparing a difference between the user metabolic rate and the updated user total energy expenditure with the result of dividing the remaining amount to lose by the remaining duration of the weight management program.

<5> The method of <1> to <4> wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

<6> The method of <1> to <5>, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
   i. a first behavioral segment score obtained by applying a first behavioral segmentation function to the behavioral data;
   ii. a second behavioral segment score obtained by applying a second behavioral segmentation function to the behavioral data; and
   iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
   i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and
   ii. assigning the user to an attitudinal segment corresponding to a maximum attitudinal segment score from the plurality of attitudinal segment scores.

<7> The method of <1> to <6> wherein:
a. the user recommended exercise amount is a recommendation of a daily amount of calories to expend in exercise;
b. the user recommended meal amount is a recommendation of a daily amount of calories to consume;
c. the user meal recommendation is a recommendation taken from the set of recommendations consisting of:
   i. the user recommended meal amount;
   ii. a menu comprising a plurality of meals consistent with the user recommended meal amount and selectable by the user; and
   iii. a menu comprising a plurality of meal plans consistent with the user recommended meal amount;
d. the user exercise recommendation is a recommendation taken from the set of recommendations consisting of:
   i. the user recommended exercise amount;
   ii. a menu comprising a plurality of exercises consistent with the user recommended exercise amount and selectable by the user; and
   iii. a menu comprising a plurality of exercise plans consistent with the user recommended exercise amount.

<8> A non-transitory computer readable medium having stored thereon a set of instruction operable to configure a computer to perform a set of acts comprising:
a. calculating a minimum exercise amount based on an initial set of health data for a user;
b. determining a user segment based on a set of segmentation data for the user;
c. determining a user recommended exercise amount based on applying an exercise modification factor to the minimum exercise amount, wherein the exercise modification factor corresponds to the user segment;
d. storing the user recommended exercise amount; and
e. displaying a user exercise recommendation based on the user recommended exercise amount.

<9> The non-transitory computer readable medium of <8>, wherein the set of acts further comprises:
a. determining, based on the initial set of health data for the user, a user total energy expenditure and a user calorie reduction amount;
b. setting a user recommended caloric balance equal to the user total energy expenditure minus the user calorie reduction amount;
c. determining a user recommended meal amount based on adding the user recommended exercise amount to the user recommended caloric balance;
d. storing the user recommended meal amount; and
e. displaying a user meal recommendation based on the user recommended meal amount.

<10> The non-transitory computer readable medium of <8> or <9>, wherein the set of acts further comprises:
a. receiving an updated set of health data for the user;
b. determining, based on the updated set of health data for the user, an updated user total energy expenditure and an updated user calorie reduction amount;
c. setting an updated user recommended caloric balance equal to the updated user total energy expenditure minus the updated user calorie reduction amount;
d. determining an updated user recommended exercise amount based on the updated set of health data for the user;

e. determining an updated user recommended meal amount based on adding the updated user recommended exercise amount to the updated user recommended caloric balance;
f. storing the updated user recommended meal amount and the updated user recommended exercise amount;
g. displaying an updated user meal recommendation based on the updated user recommended meal amount and an updated user exercise recommendation based on the updated user recommended exercise amount; and
h. repeating steps a-g one or more times during a weight management program.

<11> The non-transitory computer readable medium of <8> to <10>, wherein determining, based on the updated set of health data for the user, the updated user total energy expenditure and the updated user calorie reduction amount comprises:
a. determining the updated user total energy expenditure by applying an enhancement to a user metabolic rate determined based on:
  i. a weight from the updated set of health data for the user;
  ii. a height from the initial set of health data for the user;
  iii. an age for the user; and
  iv. a gender from the initial set of health data for the user;
b. setting a remaining amount to lose based on a difference between:
  i. a target weight determined at the inception of the weight management program based on the initial set of health data; and
  ii. the weight from the updated set of health data for the user; and
c. determining the updated user calorie reduction amount based on:
  i. a result of dividing the remaining amount to lose by a remaining duration of the weight management program; and
  ii. comparing a difference between the user metabolic rate and the updated user total energy expenditure with the result of dividing the remaining amount to lose by the remaining duration of the weight management program.

<12> The non-transitory computer readable medium of <8> to <11> wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

<13> The non-transitory computer readable medium of <8> to <12>, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
  i. a first behavioral segment score obtained by applying a first behavioral segmentation function to the behavioral data;
  ii. a second behavioral segment score obtained by applying a second behavioral segmentation function to the behavioral data; and
  iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
  i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and
  ii. assigning the user to an attitudinal segment corresponding to a maximum attitudinal segment score from the plurality of attitudinal segment scores.

<14> A machine comprising:
A. a server;
B. a terminal computer located remotely from the server; and
C. a database located remotely from the terminal computer and communicatively coupled to the server;
wherein the server is configured with a set of instructions stored on a non-transitory computer readable medium and operable to configure the server to perform a set of acts comprising:
a. calculating a minimum exercise amount based on an initial set of health data for a user;
b. determining a user segment based on a set of segmentation data for the user;
c. determining a user recommended exercise amount based on applying an exercise modification factor to the minimum exercise amount, wherein the exercise modification factor corresponds to the user segment;
d. storing the user recommended exercise amount in the database; and
e. displaying, via the terminal computer, a user exercise recommendation based on the user recommended exercise amount.

<15> The machine of <14>, wherein the set of acts further comprises:
a. determining, based on the initial set of health data for the user, a user total energy expenditure and a user calorie reduction amount;
b. setting a user recommended caloric balance equal to the user total energy expenditure minus the user calorie reduction amount;
c. determining a user recommended meal amount based on adding the user recommended exercise amount to the user recommended caloric balance;
d. storing the user recommended meal amount; and
e. displaying a user meal recommendation based on the user recommended meal amount.

<16> The machine of <14> or <15>, wherein the set of acts further comprises:
a. receiving an updated set of health data for the user;
b. determining, based on the updated set of health data for the user, an updated user total energy expenditure and an updated user calorie reduction amount;

c. setting an updated user recommended caloric balance equal to the updated user total energy expenditure minus the updated user calorie reduction amount;
d. determining an updated user recommended exercise amount based on the updated set of health data for the user;
e. determining an updated user recommended meal amount based on adding the updated user recommended exercise amount to the updated user recommended caloric balance;
f. storing the updated user recommended meal amount and the updated user recommended exercise amount;
g. displaying an updated user meal recommendation based on the updated user recommended meal amount and an updated user exercise recommendation based on the updated user recommended exercise amount; and
h. repeating steps a-g one or more times during a weight management program.

<17> The machine of <14> to <16>, wherein determining, based on the updated set of health data for the user, the updated user total energy expenditure and the updated user calorie reduction amount comprises:
a. determining the updated user total energy expenditure by applying an enhancement to a user metabolic rate determined based on:
  i. a weight from the updated set of health data for the user;
  ii. a height from the initial set of health data for the user;
  iii. an age for the user; and
  iv. a gender from the initial set of health data for the user;
b. setting a remaining amount to lose based on a difference between:
  i. a target weight determined at the inception of the weight management program based on the initial set of health data; and
  ii. the weight from the updated set of health data for the user; and
c. determining the updated user calorie reduction amount based on:
  i. a result of dividing the remaining amount to lose by a remaining duration of the weight management program; and
  ii. comparing a difference between the user metabolic rate and the updated user total energy expenditure with the result of dividing the remaining amount to lose by the remaining duration of the weight management program.

<18> The machine of <14> to <17> wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

<19> The machine of <14> to <18>, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
  i. a first behavioral segment score obtained by applying a first behavioral segmentation function to the behavioral data;
  ii. a second behavioral segment score obtained by applying a second behavioral segmentation function to the behavioral data; and
  iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
  i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and
  ii. assigning the user to an attitudinal segment corresponding to a maximum attitudinal segment score from the plurality of attitudinal segment scores.

<20> The machine of <14> to <19>, wherein the server is configured to operate as:
a. a means for determining a user segment; and
b. a means for determining a user recommended exercise amount.

What is claimed is:
1. A method comprising:
a. at a server, receiving an initial set of health data for a user and a set of segmentation data for the user;
b. calculating a minimum exercise amount based on the initial set of health data for the user;
c. determining a user segment based on the set of segmentation data for the user;
d. determining a user recommended exercise amount based on applying an exercise modification factor to the minimum exercise amount, wherein the exercise modification factor corresponds to the user segment;
e. storing the user recommended exercise amount in a database communicatively connected to the server;
f. displaying, via a terminal computer, a user exercise recommendation based on the user recommended exercise amount;
g. determining, based on the initial set of health data for the user, a user total energy expenditure and a user calorie reduction amount;
h. setting a user recommended caloric balance equal to the user total energy expenditure minus the user calorie reduction amount;
i. determining a user recommended meal amount based on adding the user recommended exercise amount to the user recommended caloric balance;
j. storing the user recommended meal amount in the database; and
k. displaying a user meal recommendation based on the user recommended meal amount.

2. The method of claim 1, further comprising:
a. receiving an updated set of health data for the user;

b. determining, based on the updated set of health data for the user, an updated user total energy expenditure and an updated user calorie reduction amount;
c. setting an updated user recommended caloric balance equal to the updated user total energy expenditure minus the updated user calorie reduction amount;
d. determining an updated user recommended exercise amount based on the updated set of health data for the user;
e. determining an updated user recommended meal amount based on adding the updated user recommended exercise amount to the updated user recommended caloric balance;
f. storing the updated user recommended meal amount and the updated user recommended exercise amount in the database;
g. displaying an updated user meal recommendation based on the updated user recommended meal amount and an updated user exercise recommendation based on the updated user recommended exercise amount; and
h. repeating steps a-g one or more times during a weight management program.

3. The method of claim 2, wherein determining, based on the updated set of health data for the user, the updated user total energy expenditure and the updated user calorie reduction amount comprises:
a. determining the updated user total energy expenditure by applying an enhancement to a user metabolic rate determined based on:
   i. a weight from the updated set of health data for the user;
   ii. a height from the initial set of health data for the user;
   iii. an age for the user; and
   iv. a gender from the initial set of health data for the user;
b. setting a remaining amount to lose based on a difference between:
   i. a target weight determined at the inception of the weight management program based on the initial set of health data; and
   ii. the weight from the updated set of health data for the user; and
c. determining the updated user calorie reduction amount based on:
   i. a result of dividing the remaining amount to lose by a remaining duration of the weight management program; and
   ii. comparing a difference between the user metabolic rate and the updated user total energy expenditure with the result of dividing the remaining amount to lose by the remaining duration of the weight management program.

4. The method of claim 2 wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

5. The method of claim 1, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
   i. a first behavioral segment score obtained by applying a first behavioral segmentation function to the behavioral data;
   ii. a second behavioral segment score obtained by applying a second behavioral segmentation function to the behavioral data; and
   iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
   i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and
   ii. assigning the user to an attitudinal segment corresponding to a maximum attitudinal segment score from the plurality of attitudinal segment scores.

6. The method of claim 1 wherein:
a. the user recommended exercise amount is a recommendation of a daily amount of calories to expend in exercise;
b. the user recommended meal amount is a recommendation of a daily amount of calories to consume;
c. the user meal recommendation is a recommendation taken from the set of recommendations consisting of:
   i. the user recommended meal amount;
   ii. a menu comprising a plurality of meals consistent with the user recommended meal amount and selectable by the user; and
   iii. a menu comprising a plurality of meal plans consistent with the user recommended meal amount;
d. the user exercise recommendation is a recommendation taken from the set of recommendations consisting of:
   i. the user recommended exercise amount;
   ii. a menu comprising a plurality of exercises consistent with the user recommended exercise amount and selectable by the user; and
   iii. a menu comprising a plurality of exercise plans consistent with the user recommended exercise amount.

7. A non-transitory computer readable medium having stored thereon a set of instruction operable to configure a computer to perform a set of acts comprising:
a. calculating a minimum exercise amount based on an initial set of health data for a user b. determining a user segment based on a set of segmentation data for the user;
c. determining a user recommended exercise amount based on applying an exercise modification factor to the minimum exercise amount, wherein the exercise modification factor corresponds to the user segment;
d. storing the user recommended exercise amount;
e. displaying a user exercise recommendation based on the user recommended exercise amount;
f. determining, based on the initial set of health data for the user, a user total energy expenditure and a user calorie reduction amount;
g. setting a user recommended caloric balance equal to the user total energy expenditure minus the user calorie reduction amount;
h. determining a user recommended meal amount based on adding the user recommended exercise amount to the user recommended caloric balance;
i. storing the user recommended meal amount; and
j. displaying a user meal recommendation based on the user recommended meal amount.

8. The non-transitory computer readable medium of claim 7, wherein the set of acts further comprises:
a. receiving an updated set of health data for the user;
b. determining, based on the updated set of health data for the user, an updated user total energy expenditure and an updated user calorie reduction amount;
c. setting an updated user recommended caloric balance equal to the updated user total energy expenditure minus the updated user calorie reduction amount;
d. determining an updated user recommended exercise amount based on the updated set of health data for the user;
e. determining an updated user recommended meal amount based on adding the updated user recommended exercise amount to the updated user recommended caloric balance;
f. storing the updated user recommended meal amount and the updated user recommended exercise amount;
g. displaying an updated user meal recommendation based on the updated user recommended meal amount and an updated user exercise recommendation based on the updated user recommended exercise amount; and
h. repeating steps a-g one or more times during a weight management program.

9. The non-transitory computer readable medium of claim 8, wherein determining, based on the updated set of health data for the user, the updated user total energy expenditure and the updated user calorie reduction amount comprises:
a. determining the updated user total energy expenditure by applying an enhancement to a user metabolic rate determined based on:
  i. a weight from the updated set of health data for the user;
  ii. a height from the initial set of health data for the user;
  iii. an age for the user; and
  iv. a gender from the initial set of health data for the user;
b. setting a remaining amount to lose based on a difference between:
  i. a target weight determined at the inception of the weight management program based on the initial set of health data; and
  ii. the weight from the updated set of health data for the user; and
c. determining the updated user calorie reduction amount based on:
  i. a result of dividing the remaining amount to lose by a remaining duration of the weight management program; and
  ii. comparing a difference between the user metabolic rate and the updated user total energy expenditure with the result of dividing the remaining amount to lose by the remaining duration of the weight management program.

10. The non-transitory computer readable medium of claim 8 wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

11. The non-transitory computer readable medium of claim 7, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
  i. a first behavioral segment score obtained by applying a first behavioral segmentation function to the behavioral data;
  ii. a second behavioral segment score obtained by applying a second behavioral segmentation function to the behavioral data; and
  iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
  i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and
  ii. assigning the user to an attitudinal segment corresponding to a maximum attitudinal segment score from the plurality of attitudinal segment scores.

12. A machine comprising:
A. a server;

B. a terminal computer located remotely from the server; and
C. a database located remotely from the terminal computer and communicatively coupled to the server;
wherein the server is configured with a set of instructions stored on a non-transitory computer readable medium and operable to configure the server to perform a set of acts comprising:
a. calculating a minimum exercise amount based on an initial set of health data for a user
b. determining a user segment based on a set of segmentation data for the user;
c. determining a user recommended exercise amount based on applying an exercise modification factor to the minimum exercise amount, wherein the exercise modification factor corresponds to the user segment;
d. storing the user recommended exercise amount in the database;
e. displaying, via the terminal computer, a user exercise recommendation based on the user recommended exercise amount;
f. determining, based on the initial set of health data for the user, a user total energy expenditure and a user calorie reduction amount;
g. setting a user recommended caloric balance equal to the user total energy expenditure minus the user calorie reduction amount;
h. determining a user recommended meal amount based on adding the user recommended exercise amount to the user recommended caloric balance;
i. storing the user recommended meal amount; and
j. displaying a user meal recommendation based on the user recommended meal amount.

13. The machine of claim 12, wherein the set of acts further comprises:
a. receiving an updated set of health data for the user;
b. determining, based on the updated set of health data for the user, an updated user total energy expenditure and an updated user calorie reduction amount;
c. setting an updated user recommended caloric balance equal to the updated user total energy expenditure minus the updated user calorie reduction amount;
d. determining an updated user recommended exercise amount based on the updated set of health data for the user;
e. determining an updated user recommended meal amount based on adding the updated user recommended exercise amount to the updated user recommended caloric balance;
f. storing the updated user recommended meal amount and the updated user recommended exercise amount;
g. displaying an updated user meal recommendation based on the updated user recommended meal amount and an updated user exercise recommendation based on the updated user recommended exercise amount; and
h. repeating steps a-g one or more times during a weight management program.

14. The machine of claim 13, wherein determining, based on the updated set of health data for the user, the updated user total energy expenditure and the updated user calorie reduction amount comprises:
a. determining the updated user total energy expenditure by applying an enhancement to a user metabolic rate determined based on:
i. a weight from the updated set of health data for the user;
ii. a height from the initial set of health data for the user;
iii. an age for the user; and
iv. a gender from the initial set of health data for the user;
b. setting a remaining amount to lose based on a difference between:
i. a target weight determined at the inception of the weight management program based on the initial set of health data; and
ii. the weight from the updated set of health data for the user; and
c. determining the updated user calorie reduction amount based on:
i. a result of dividing the remaining amount to lose by a remaining duration of the weight management program; and
ii. comparing a difference between the user metabolic rate and the updated user total energy expenditure with the result of dividing the remaining amount to lose by the remaining duration of the weight management program.

15. The machine of claim 13 wherein determining the updated user recommended exercise amount based on the updated set of health data for the user comprises performing a process taken from a set of processes consisting of:
a. based on a lack of exercise data from the updated set of health data for the user, setting the updated user recommended exercise amount by applying the exercise modification factor to a minimum exercise amount determined based on the updated set of health data for the user;
b. based on an actual exercise amount for the user being greater than or equal to a previous recommended exercise amount, setting the updated user recommended exercise amount equal to the actual exercise amount for the user; and
c. based on the user failing to meet the previous recommended exercise amount, setting the updated user recommended exercise amount equal to the minimum exercise amount determined based on the updated set of health data for the user.

16. The machine of claim 12, wherein determining a user segment based on the set of segmentation data for the user comprises:
a. determining a plurality of behavioral segment scores based on behavioral segmentation data from the set of segmentation data for the user, wherein the behavioral segmentation data from the set of segmentation data for the user indicates the user's focus on exercise, diet and medication when addressing health issues, and wherein the plurality of behavioral segment scores comprises:
i. a first behavioral segment score obtained by applying a first behavioral segmentation function to the behavioral data;
ii. a second behavioral segment score obtained by applying a second behavioral segmentation function to the behavioral data; and
iii. a third behavioral segment score obtained by applying a third behavioral segment function to the behavioral data;
b. assigning the user to a behavioral segment corresponding to a maximum behavioral segment score from the plurality of behavioral segment scores;
c. based on identifying a need for additional segmentation:
i. determining a plurality of attitudinal segment scores based on the behavioral segmentation data from the set of segmentation data for the user and on attitudinal segmentation data from the set of segmentation data for the user, wherein each attitudinal segment score from the plurality of attitudinal segment scores is obtained by applying a corresponding attitudinal segmentation function to the segmentation data for the user; and ii. assigning the user to an attitudinal segment corresponding to a maximum attitudinal segment score from the plurality of attitudinal segment scores.

17. The machine of claim 12, wherein the server is configured to operate as:

a. a means for determining a user segment; and b. a means for determining a user recommended exercise amount.

* * * * *

UNITED STATES PATENT AND TRADEMARK OFFICE
CERTIFICATE OF CORRECTION

Page 1 of 1

PATENT NO.         : 9,298,888 B2
APPLICATION NO.    : 13/896534
DATED              : March 29, 2016
INVENTOR(S)        : Kanji Akai et al.

It is certified that error appears in the above-identified patent and that said Letters Patent is hereby corrected as shown below:

In the Claims

Column 30, Claim 7, line 67, reads "...health data for a user..."; which should be deleted and replaced with "...health data for a user;..."

Signed and Sealed this
Seventh Day of June, 2016

Michelle K. Lee
*Director of the United States Patent and Trademark Office*